(12) United States Patent  
Steinmetz et al.

(10) Patent No.: US 8,703,970 B2  
(45) Date of Patent: Apr. 22, 2014

(54) COMPOUNDS HAVING PHOTOCHEMICALLY REMOVABLE PROTECTING GROUPS BASED ON AN ELECTROCYCLIC REACTION BETWEEN A CHROMOPHORE ATTACHED VIA AN ANILIDE GROUP TO A BENZOTHIOPHENE RING

(71) Applicant: Marquette University, Milwaukee, WI (US)

(72) Inventors: Mark G. Steinmetz, Whitefish Bay, WI (US); Majher I. Sarker, Milwaukee, WI (US); Tasnuva Shahrin, Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 0 days.

(21) Appl. No.: 13/779,141

(22) Filed: Feb. 27, 2013

(65) Prior Publication Data  
US 2013/0231484 A1   Sep. 5, 2013

Related U.S. Application Data

(60) Provisional application No. 61/605,406, filed on Mar. 1, 2012.

(51) Int. Cl.  
*C07D 333/00* (2006.01)  
*C07D 409/00* (2006.01)  
*C07D 495/00* (2006.01)  
*C07D 333/22* (2006.01)  
*A01N 43/12* (2006.01)  
*A01N 43/06* (2006.01)  
*A01N 43/18* (2006.01)  
*A01N 43/14* (2006.01)  
*A61K 31/38* (2006.01)

(52) U.S. Cl.  
USPC .................. 549/57; 549/59; 549/72; 549/43; 549/48; 514/443; 514/445; 514/437; 514/432

(58) Field of Classification Search  
USPC ......................................... 549/57  
See application file for complete search history.

(56) References Cited

FOREIGN PATENT DOCUMENTS

WO      WO 2004089529      * 10/2004

OTHER PUBLICATIONS

Wermuth; "Preparation of Water-Soluble Compounds by Covalent Attachment of Solubilizing Moieties" in Practice of Medicinal Chemistry, Third Ed, 2008, Elsevier, chapter 38.*  
Tani; Chem. Lett. 2011, 40, 1267-1268.*  
Coleman; J. Org. Chem. 2002, 67, 7641-7648.*  
Furuta et al., "7-hydroxycoumarin-4-ylmethyls: Photolabile protecting groups with biologically useful cross-sections for two photon photolysis", Proc. Natl. Acad. Sci, USA, 1999, 96, 1193-1200.  
Lee et al., "Illuminating the chemistry of life: design, synthesis, and applications of "caged" and related photoresponsive compounds", ACS Chem. Biol. 2009, 4, 409-427.

(Continued)

*Primary Examiner* — John Mabry  
*Assistant Examiner* — Daniel Carcanague  
(74) *Attorney, Agent, or Firm* — Andrus Intellectual Property Law, LLP

(57) ABSTRACT

Disclosed herein are compounds having photoremovable protecting groups which are removed after the compounds absorbs light of a given wavelength and undergo an electrocyclic reaction between a chromophore in the compound attached via an anilide to a benzothiophene ring.

18 Claims, 4 Drawing Sheets

7 (LG⁻ = Cl⁻)

8 (LG⁻ = Cl⁻)

9 (LG⁻ = Cl⁻, HS⁻, PhS⁻, PhCH₂S⁻)    10 (LG⁻ = Cl⁻)

(56) References Cited

OTHER PUBLICATIONS

Sarker et al., Photochemical electrocyclic ring closure and leaving group expulsion from N-(9-oxothioxanthenyl) benzothiophene carboxamides, Photochem Photobiol Sci., 2013, (2):309-22.
Stensrud et al., "Competing pathways in the photo-Favorskii rearrangement and release of esters: studies on fluorinated p-hydroxyphenacyl-caged GABA and glutamate phototriggers", J. Org. Chem. 2009, 74, 5219-5227.
Walker et al., "Signaling pathways underlying eosinophil cell motility revealed by using caged peptides", Proc. Natl. Acad. Sci USA, 1998, 95, 1568-1573.
Zhao et al., "Cysteine-activated hydrogen sulfide (H2S) donors", J. Am. Chem. Soc. 2011, 133, 15-17.
ST075284—Compound Summary, accessed on Dec. 12, 2011.
Beltowski, "Hypoxia in the Renal Medulla: Implications for Hydrogen Sulfide Signaling", The Journal of Pharmacology and Experimental Therapeutics, 2010, 334:358-363.
Chang et al., "Caged catalytic subunit of cAMP-dependent protein kinase", J. Am. Chem. Soc., 1998, 120:7661-7662.
Chen et al., "Photochemical cyclization with release of carboxylic acis and phenol from pyrrolidino-substituted 1,4-benzoquinones using visible light", Organic Letters, 2005, 7(17):3729-3732.
Chen et al., "Photoactivation of amino-substituted 1,4-benzoquinones for release of carboylate and phenolate leaving groups using visible light", J. Org. Chem., 2006, 71:6053-6060.
Cheng et al., "Photolysis of γ-(α-Carboxy-2-nitrobenzyl)-L-glutamic acid investigated in the microsecond time scale by time-resolved FTIR", J. Am. Chem. Soc., 2002, 124:7676-7677.
Cohen et al., "Competitive processes in retardation by mercaptans of photreduction by alcohols", Journal of the American Chemical Society, Mar. 28, 1979, 101(7):1827.
Davis et al., "Substituent effects on the sensitivity of a quinoline photoremovable protecting group to one- and two-photon excitation", J. Org. Chem., 2009, 74:1721-1729.
Fukui, "The path of chemical reactions—the IRC approach", Accounts of Chemical Reactions, Dec. 1981, 14 (12):363.
Gadalla et al., "Hydrogen sulfide as a gasotransmitter", Journal of Neurochemistry, 2010, 113:14-26.
Guttenplan et al., "Quenching and reduction of photoexcited benzophenone by thioethers and mercaptans", J. Org. Chem., 1973, 38(11):2001.
Hagen et al., "Highly efficient and ultrafast phototriggers for cAMP and cGMP by using long-wavelength UV/Vis-activation", Angew. Chem. Int. Ed., 2001, 40(6):1045.
Il'Ichev et al., "Photochemical reaction mechanisms of 2-nitrobenzyl compounds: methyl ethers and caged ATP", J. Am. Chem. Soc., 2004, 126:4581-4595.
Inbar et al., "Quenching and radical formation in the reaction of photoexcited benzophenone with thiols and thioethers (sulfides). Nanosecond flash studies", J. Am. Chem. Soc., 1982, 104:1679-1682.
Jia et al., "Photochemical elimination of leaving groups from Zwitterionic intermediates generated via electrocyclic ring closure of α,β-unsaturated anilides", J. Org. Chem., 2008, 73:8867-8879.
Ma et al., "Photochemical cleavage and release of carboxylic acids from α-keto amides", Organic Letters, 2003, 5 (1):71-74.
Ma et al., "Substituent effects on competitive release of phenols and 1,3-rearrangement in α-keto amide photochemistry", Organic Letters, 2004, 6(4):629-632.
Ma et al., "Photochemical cleavage and release of carboxylic acids from α-keto amides", J. Organic Chemistry, 2005, 71:4431-4442.
Ma et al., "Photochemical cleavage and release of para-substituted phenols from α-keto amides", J. Org. Chem., 2006, 71:4206-4215.

Mayer et al., "Biologically active molecules with a 'light switch'", Angew. Chem. Int. Ed., 2006, 45:4900-4921.
Miguel et al., "Wavelength-selective caged surfaces: how many functional levels are possible?", J. Am. Chem. Soc., 2011, 133:5380-5388.
Montanari et al., "Pathways of nitrosobenzene reduction by thiols in alcoholic media", J. Org. Chem., 1999, 64:3422-3428.
Moon et al., "Synthesis of some 2-substituted-thioxanthones", J. Heterocyclic Chem., 1999, 36:793.
Neumann et al., "Photophysics and photoreactivity of substituted thioxanthones", J. Chem. Soc., Faraday Trans., 1997, 93(8):1517-1521.
Pechlivanidis et al., "Paracyclophanes: Extending the bridges. Synthesis", Eur. J. Org. Chem., 2009, 223-237.
Perdew et al., "Generalized gradient approximation made simple", Physical Review Letters, Oct. 28, 1996, 77 (18):3865.
Pinheiro et al., "pH effect on the photochemistry of 4-methylcoumarin phosphate esters: Caged-phosphate case study", J. Phys. Chem. A, 2010, 114:12795-12803.
Rubio-Pons et al., "A butterfly like motion as a clue to the photophysics of thioxanthone", Journal of Photochemistry and Photobiology A: Chemistry, 2006, 179:298-304.
Sarker et al., "Photochemical eliminations involving zwitterionic intermediates generated via electrocyclic ring closure of benzothiophene carboxanilides", Organic Letters, 2011, 13(5):872-875.
Scalmani et al., "Continuous surface charge polarizable continuum models of solvation. I. General Formalism", J. Chem. Phys., 2010, 132:114110.
Schmidt et al., "Mechanism of photocleavage of (Coumarin-4-yl)methyl esters", J. Phys. Chem. A, 2007, 111:5768-5774.
Seixas De Melos et al., "Photochemistry and photophysics of thiencarbazoles", Photochemistry and Photobiology, 2003, 77(2):121-128.
Specht et al., "p-Hydroxyphenacyl bromide as photoremoveable thiol label: a potential phototrigger for thiol-containing biomolecules", Tetrahedron Letters, 2002, 43:8947-8950.
Steinmetz et al., "Photochemistry of a trisilane substituted by a pendant p-Cyanostilbene electron acceptor chromophore", J. Org. Chem., 1999, 64:2057-2065.
Tomasi et al., "The IEF version of the PCM solvation method: an overview of a new method addressed to study molecular solutes at the QM ab initio level", Journal of Molecular Structure, 1999, 464:211-226.
Tomasi et al., "Quantum mechanical continuum solvation models", Chem. Rev., 2005, 105:2999-3093.
Van Delden et al., "Photochemical and thermal isomerization processes of a chiral auxiliary based donor-acceptor substituted chiroptical molecular switch: convergent synthesis, improved resolution and switching properties", Chem. Eur. J., 2003, 2003, 9:2845-2853.
Walker et al., "Rapid release of an α-adrenergic receptor ligand from photolabile analogues", Biochemistry, 1993, 32:1338-1345.
Warther et al., "Two-photon uncaging: new prospects in neuroscience and cellular biology", Bioorganic & Medicinal Chemistry, 2010, 18:7753-7758.
Wex et al., "Altering the emission behavior with the turn of a thiophene ring: The photophysics of condensed ring systems of alternating benzenes and thiophenes", J. Phys. Chem. A, 2006, 110:13754-13758.
Wright et al., "The preparation of 3-chlorobenzo[b]thiophene derivatives from cinnamic acids", J. Heterocyclic Chem. 1971, 8:711-714.
Zhang et al., "Computation of large systems with economic basis set: systems involving weak sodium-organic interaction", Chemical Physics Letters, 2000, 330:484-490.

* cited by examiner

1

COMPOUNDS HAVING PHOTOCHEMICALLY REMOVABLE PROTECTING GROUPS BASED ON AN ELECTROCYCLIC REACTION BETWEEN A CHROMOPHORE ATTACHED VIA AN ANILIDE GROUP TO A BENZOTHIOPHENE RING

CROSS-REFERENCE TO RELATED PATENT APPLICATIONS

The present application claims the benefit of priority under 35 U.S.C. §119(e) to U.S. Provisional Patent Application No. 61/605,406, filed on Mar. 1, 2012, the content of which is incorporated herein by reference in its entirety.

STATEMENT REGARDING FEDERALLY SPONSORED RESEARCH OR DEVELOPMENT

This invention was made with government support under CHE 1055339 awarded by the National Science Foundation. The government has certain rights in the invention.

BACKGROUND

The field of the invention relates to compounds having photochemically removable protecting groups. Photochemically removable protecting groups that release biologically active molecules upon exposure to light, otherwise referred to as "cage compounds," have been widely used in biological applications and physiological studies.[1,2] However, the cage compounds typically used have certain drawbacks, which may not always be obvious. In particular, UV light is most often used to effect the photochemical release of the biologically active molecule, but may cause cellular damage and mortality.[3] Cage compounds may undergo premature hydrolytic or even enzymatic release of the bioeffector in living cells.[1] Finally, the types of bioeffector leaving groups that can be photochemically released from the photoremovable protecting group are all too often limited to rather weak bases such as carboxylate groups and phosphate esters. Improved compounds having photochemically removable protecting groups are desirable. Especially, compounds that undergo photochemical release upon exposure to light at relatively long wavelengths that extend into the visible range.

SUMMARY

Disclosed herein are compounds having photoremovable protecting groups which are removed after the compounds absorbs light of a given wavelength and undergo an electrocyclic reaction between a chromophore in the compound attached via an anilide group to a benzothiophene ring.

The disclosed compounds may have a formula:

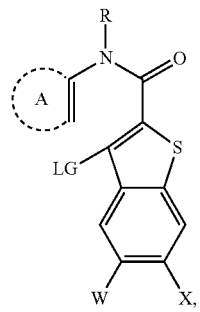

or a zwitterion thereof. Typically, the compounds are soluble in aqueous solution. The substituents W and X are hydrogen or —COOY where at least one of W and X is —COOY. Substituent COOY typically is a group which increases the water solubility of the compound such as a carboxyl group or an alkyl ester which may be hydrolyzed to provide a carboxyl group. As such, Y typically is H or a $C_1$-$C_6$ alkyl, which may be straight chain or branched and more typically methyl (i.e., W and X independently are selected from hydrogen, a carboxyl group, or an ester group, with the proviso that at least one of W and X is a carboxyl group or an ester group). The "photoremovable group" or "leaving group" LG typically is a nucleophile or base or anion such as $Cl^-$, $PhCH_2CO_2^-$, $PhS^-$, $PhCH_2S^-$, $PhO^-$, $HO^-$, or $HS^-$. Substituent R typically is $C_1$-$C_6$ alkyl, which may be straight chain or branched and more typically methyl. Substituent "A" typically is a chromophore comprising 1, 2, 3, or more, 5- or 6-membered aromatic rings, which optionally include one or more heteroatoms and which optionally are substituted at one or more positions, for example with a halogen. The substituent A typically absorbs light and reacts with the LG carbon atom in an electrocyclic reaction to form a compound having a formula:

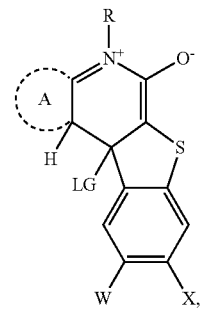

which may be referred to as a "zwitterionic intermediate." Subsequently, LG is photolyzed from the zwitterionic intermediate as discussed herein to form a compound having a formula:

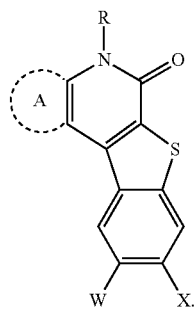

In the disclosed compounds, substituent A typically is a chromophore which absorbs light and provides a two electron component for the electrocyclic reaction. For example, substituent A may be a thioxanthene-type chromophore, a xanthene-type chromophore (e.g., a fluorescein-type chromophore or a rhodamine-type chromophore), a naphthalene-type chromophore, carbocyanine-type chromophore, dipyrromethene boron-type chromophore, coumarin-type chromophore, acridine-type chromophore, pyrene-type chromophore, DANSYL-type chromophore, and lanthanide chelate-type chromophore. Preferably, substituent A is a thioxanthene-type chromophore. In some embodiments, substituent A may be a fluorescent or phosphorescent chromophore.

In some embodiments, the disclosed compounds have a formula:

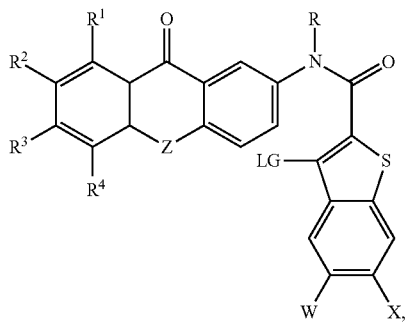

wherein Z is S or O;
$R^1$, $R^2$, $R^3$, and $R^4$ are each independently halogen or hydrogen, and R, LG, W, and X are as described herein. Specifically, the disclosed compounds may have a formula:

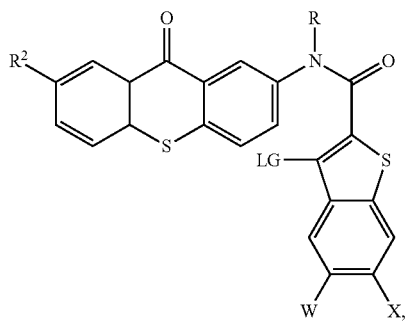

where, preferably, $R^2$ is bromine.

In other embodiments, the disclosed compounds have a formula:

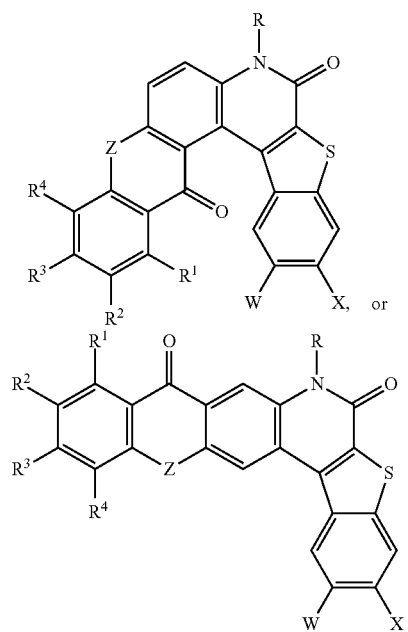

wherein Z is S or O, and
$R^1$, $R^2$, $R^3$, and $R^4$ are each independently halogen or hydrogen, and R, LG, W, and X are as described herein. Specifically, the disclosed compounds may have a formula:

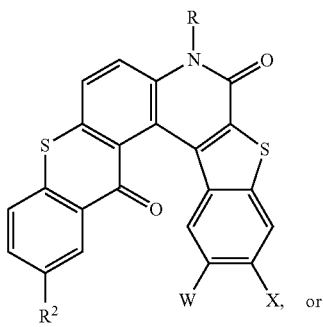

where, preferably, $R^2$ is bromine.

The disclosed compounds typically absorb light and undergo an electrocyclic reaction whereby the leaving group is photolytically released from the compound. In some embodiments, the compounds have an absorption maxima greater than about 350 nm and extending into the visible wavelengths of light (e.g., greater than about 360, 370, 380, 390, 400, 410, or 420 nm). In some embodiments, the compounds have an absorption maxima of about 350-400 nm. After the compounds have undergone the electrocyclic reaction whereby the leaving group is photolytically released from the compound, the compounds may have a higher absorption maxima, for example, an absorption maxima of about 400-450 nm.

Also disclosed are methods for performing a photolytic reaction. The methods typically include subjecting the compounds disclosed herein having a formula:

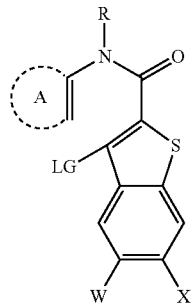

to light to produce the compounds disclosed herein having a formula:

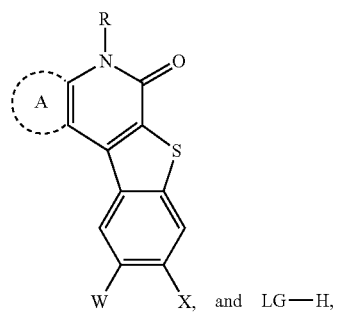

where A, R, W, X, and LG are as described herein. In the disclosed methods, the photolytic reaction typically has a yield of greater than about 80%, 85%, 90%, 95%, 96%, 97%, 98%, 99%, or 100%, after the compound has been subjected to light for a suitable period of time (e.g., for at least about 10, 30, 60, or 90 minutes). Suitable light may include light having a wavelength greater than about 350 nm and extending into the visible wavelengths of light (e.g., greater than about 360, 370, 380, 390, 400, 410, or 420 nm). In some embodiments, suitable light may include light of a wavelength between about 350-450 nm.

Also disclosed are synthesis methods for preparing the disclosed compounds having photochemically removable protecting groups with a formula:

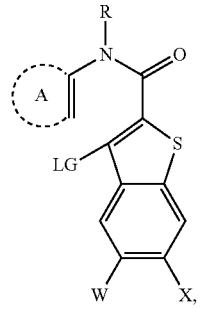

where A, R, LG, W, and X are as described herein.
The methods may include reacting a compound having a formula:

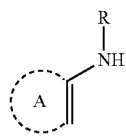

and a compound with a formula:

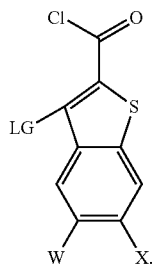

In particular, the synthesis methods may be performed to synthesis a compound having a formula:

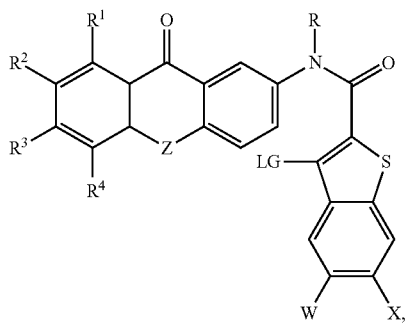

wherein R is $C_1$-$C_6$ alkyl,
Z is S or O,
$R^1$, $R^2$, $R^3$, and $R^4$ are each independently halogen or hydrogen,
W and X are hydrogen or —COOY, where Y is hydrogen or $C_1$-$C_6$ alkyl, and $LG^-$ is $Cl^-$, $PhCH_2CO_2^-$, $PhS^-$, $PhCH_2S^-$, $PhO^-$, $HO^-$, or $HS^-$.

Such methods may include reacting:
(a) a compound having a formula:

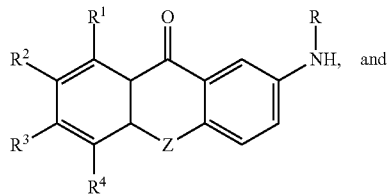

(b) a compound having a formula:

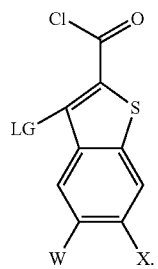

DETAILED DESCRIPTION

Figure 1:
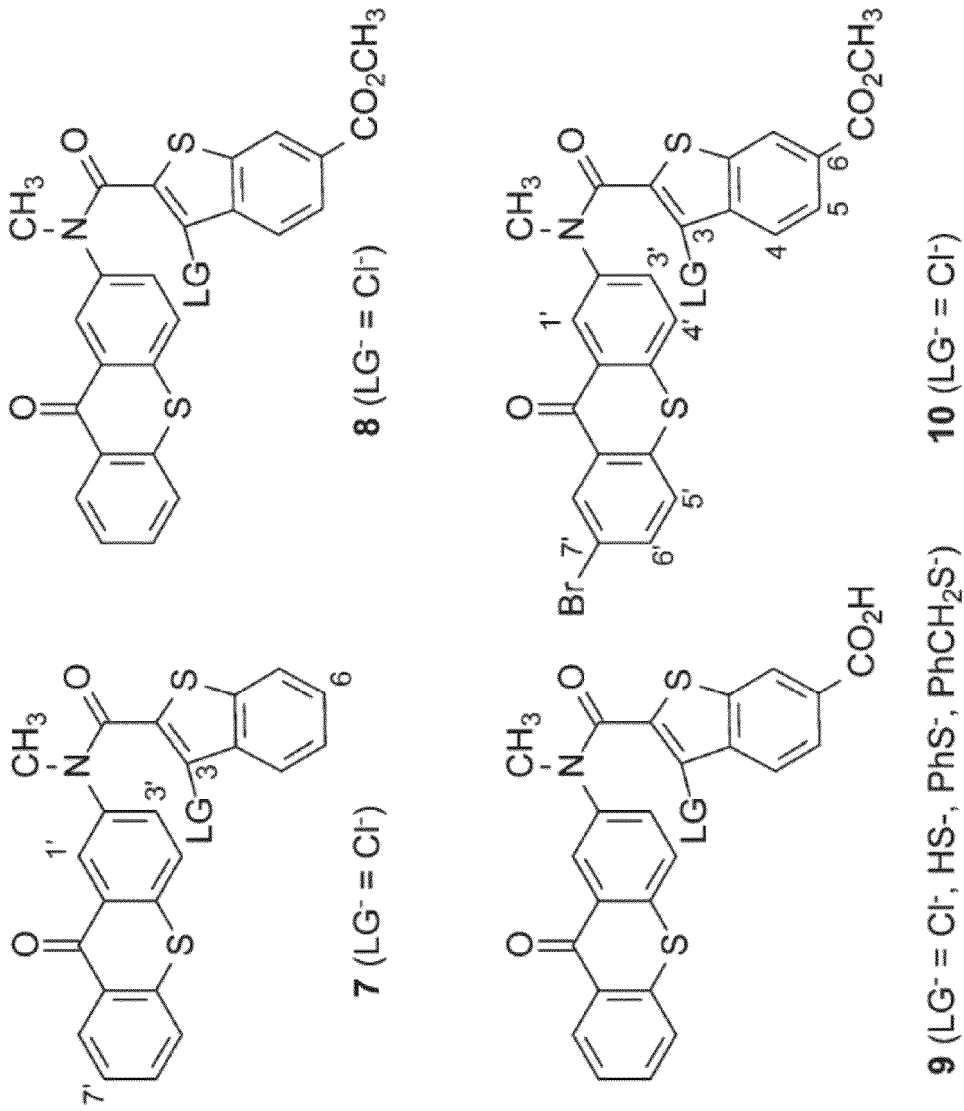
FIG. 1. illustrates compounds photolyzed in methods contemplated herein.

The disclosed subject matter further may be described utilizing terms as defined below.

Unless otherwise specified or indicated by context, the terms "a", "an", and "the" mean "one or more." For example, "a compound" should be interpreted to mean "one or more compounds."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising."

Reference is made herein to Sarker et al., "Photochemical Eliminations Involving Zwitterionic Intermediates Generated via Electrocyclic Ring Closure of Benzothiophene Carboxanilides," Org. Lett. 2011, Vol. 13, No. 5 872-875, which describes methods for synthesizing benzothiophene carboxanilides. The content of Sarker et al. 2011 is incorporated herein by reference in its entirety.

Reference also is made herein to Sarker et al., "Photochemical electrocyclic ring closure and leaving group expulsion from N-(9oxothoxanthenyl)-benzothiophene carboxamides," Photochem. Photobiol. Sci., 2013, 12, 309. The content of Sarker et al. 2013 is incorporated herein by reference in its entirety.

The compounds disclosed herein typically include a chromophore. Suitable chromophores for the compounds disclosed herein may include, but are not limited to thioxanthene-type chromophores, xanthene-type chromophores (e.g., a fluorescein-type chromophores or a rhodamine-type chromophores), a naphthalene-type chromophores, carbocyanine-type chromophores, dipyrromethene boron-type chromophores, coumarin-type chromophores, acridine-type chromophores, pyrene-type chromophores, DANSYL-type chromophores, and lanthanide chelate-type chromophores. Specific suitable chromophores may include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMIA (5-Carboxytetranethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP-Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; Euko-Light; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, WV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin ERG; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5;

PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodaminelsoThioCyanate; True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3. As used herein, a "chromophore" may include a salt of the chromophore. In some embodiments, suitable chromophores are fluorescent or phosphorescent chromophores The compounds may include a chromophore selected from the group of thioxanthene-type chromophores or xanthene-type chromophores. The group of thioxanthene-type chromophores and xanthene-type chromophores typically includes any chromophore that includes a group having the formula:

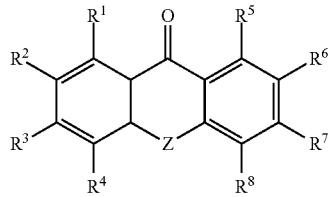

where Z is S for thioxanthene-type chromophores or O for xanthene-type chromophores. The chromophore may be substituted at one or more positions $R^1$-$R^8$, for example, with a halogen. Accordingly, in the disclosed compounds the substituent A may comprise the following structure:

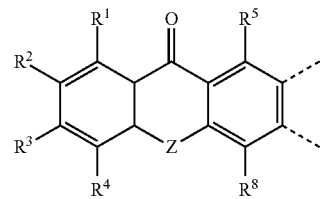

Xanthene-type fluorophores include fluorescein-type chromophores (e.g., fluoroscein and fluorescein isothiocyanate, and the like) and rhodamine-type chromophores (e.g., rhodamine, rhodamine-B, and the like).

The compounds may include a chromophore selected from the group of fluorescein-type chromophores. The group of fluorescein-type chromophores typically includes any chromophore that includes a fluorescein group having the formula:

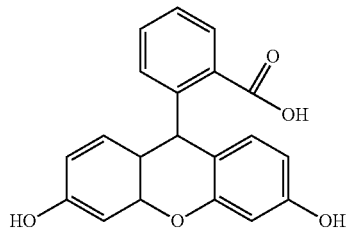 [SMILES: O=C(O)c1ccccc1C1c2ccc(O)cc2OC2C=C(O)C=CC21]

and derivatives and isomers thereof.

Fluorescein-type chromophores include fluorescein, fluorescein derivatives that include a fluorescein group, and salts thereof (e.g., 5-carboxy-2,7-dichlorofluorescein; 5-Carboxyfluorescein (5-FAM); DCFH (Dichlorodihydrofluorescein Diacetate); Fluorescein isothiocyanate (FITC); Fluorescein Diacetate, and the like). Accordingly, in the disclosed compounds the substituent A may comprise the following structure:

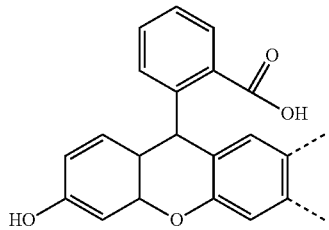

The compounds may include a chromophore selected from the group of rhodamine-type chromophores. The group of rhodamine-type chromophores typically includes any chromophore that includes a rhodamine group having the formula:

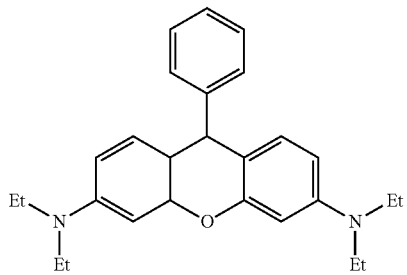 [SMILES: CCN(CC)C1=CC2Oc3cc(N(CC)CC)ccc3C(c3ccccc3)C2C=C1]

and isomers thereof. Accordingly, in the disclosed compounds the substituent A may comprise the following structure:

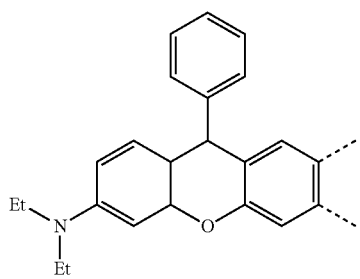

Rhodamine-type chromophores include rhodamine, rhodamine derivatives that include a rhodamine group, and salts thereof (e.g., 5-Carboxytetramethylrhodamine (5-TAMRA); 5-ROX (carboxy-X-rhodamine); 6-Carboxyrhodamine 6G; DHR (Dihydrorhodamine 123); Lissamine Rhodamine; Lissamine Rhodamine B; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Sulphorhodamine B can C; Sulphorhodamine G Extra; Tetramethylrhodamine (TRITC); X-Rhodamine; XRITC, and the like).

The compounds may include a chromophore selected from the group of the naphthalene-type chromophores. The naphthalene-type chromophores typically include any chromophore that includes a naphthalene group having the formula:

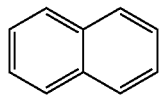

Accordingly, in the disclosed compounds the substituent A may comprise the following structure:

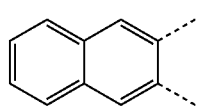

Naphthalene-type chromophores include naphthalene, IAEDANS, EDANS, and the like. Naphthalene-type chromophores may include pyrene.

EXAMPLES

The following examples are illustrative and are not intended to limit the claimed subject matter.

Photochemical Electrocyclic Ring Closure and Leaving Group Expulsion from N-(9-oxothioxanthenyl)benzothiophene Carboxamides Abstract N-(9-oxothioxanthenyl)benzothiophene carboxamides bearing leaving groups (LG$^-$=Cl$^-$, PhS$^-$, HS$^-$, PhCH$_2$S$^-$) at the C-3 position of the benzothiophene ring system photochemically cyclize with nearly quantitative release of the leaving group, LG$^-$. The LG$^-$ photoexpulsions can be conducted with 390 nm light or with a sunlamp. Solubility in 75% aqueous CH$_3$CN is achieved by introducing a carboxylate group at the C-6 position of the benzothiophene ring. The carboxylate and methyl ester derivatives regiospecifically cyclize at the more hindered C-1 position of the thioxanthone ring. Otherwise, the photocyclization favors the C-3 position of the thioxanthone. Quantum yields for reaction are 0.01-0.04, depending on LG$^-$ basicity. Electronic structure calculations for the triplet excited state show that excitation transfer occurs from the thioxanthone to the benzothiophene ring. Subsequent cyclization in the triplet excited state is energetically favorable and initially generates the triplet excited state of the zwitterionic species. Expulsion of LG$^-$ is thought to occur once this species converts to the closed shell ground state.

Introduction

Our research attempts to create derivatives of benzothiophene carboxanilides 1 (Scheme 1) that expel bioeffector leaving groups via zwitterionic intermediates 2 that are generated upon photochemical electrocyclic ring closure. Ring A subunit represents a chromophore that absorbs light at long wavelengths that extend into the visible region.

Scheme 1

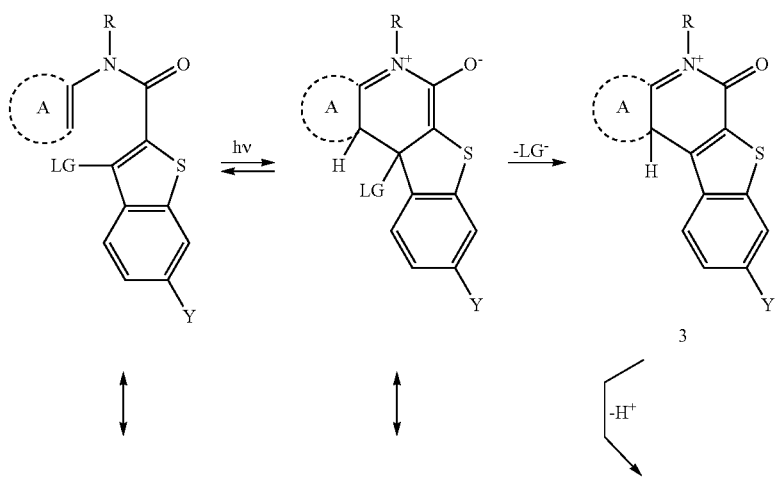

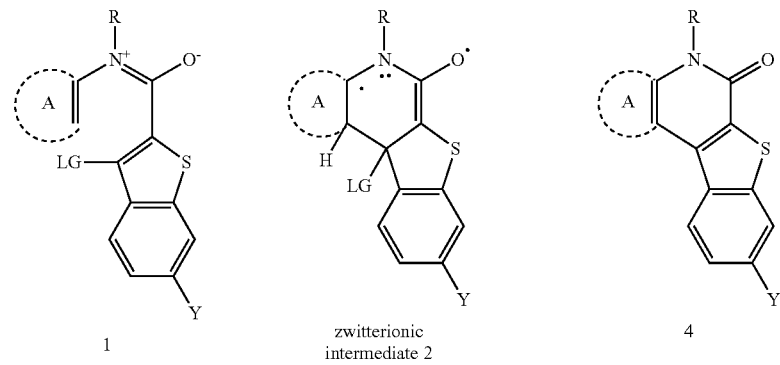

zwitterionic intermediate 2

A ⎪⎥ = chromophoric group
Y = H, CO₂CH₃, or CO₂H

The use of Scheme 1 approach to photochemically expel leaving groups from the C-3 position of the benzothiophene ring system approach was initially tested, experimentally, at short wavelengths in the UV with carboxanilides 5 (eq 1).[4] Carboxanilides 5 were found to release various leaving groups LG$^-$ that vary in basicity in essentially quantitative yields. Quantum yields decreased with increasing basicity of the LG$^-$ released over the range Φ=0.23-0.07 (LG$^-$=Cl$^-$, PhCH$_2$CO$_2^-$, PhS$^-$, PhCH$_2$S$^-$, PhO$^-$). Although the photolysis wavelength was at 310 nm in the initial studies of 5, the wavelength could be extended to 365 nm by incorporating a p-benzoyl group into the benzene ring of anilide 5.

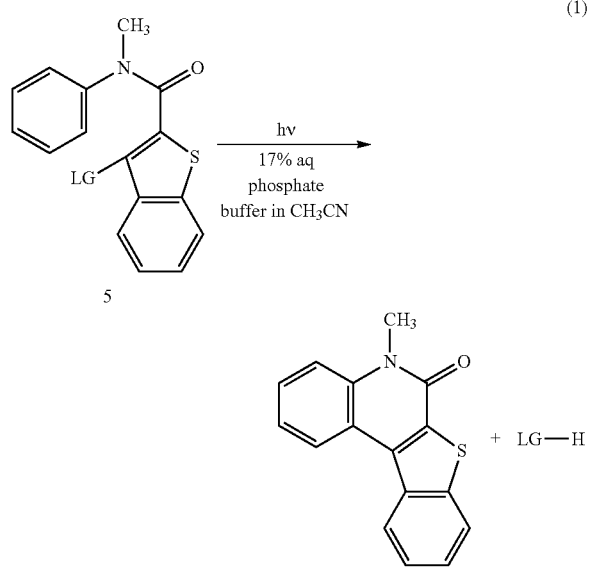

(1)

6 (91-100% yield)

LG— = Cl—, PhCH₂CO₂—, PhS—, PhCH₂S—, PhO—,
HO—

Because of the potentially modular chromophore (ring A) and the ability of the putative zwitterionic intermediate to release relatively basic leaving groups such as thiolates[5,7] and phenolates[8], i.e., side-chain groups of cysteine and tyrosine residues in peptides and proteins, the photochemical electrocyclic ring closure approach to the generation of zwitterionic intermediates appeared to be promising. In this paper we extend the absorption maximum of the chromophoric group to 385 nm by use of the thioxanthone chromophore as ring A, as shown for benzothiophene carboxamides 7-10. In addition, solubilities in aqueous buffered media are greatly improved by attaching a C-6 carboxylate group (Y=CO$_2$H) in to the benzothiophene ring system.

The leaving groups LG$^-$ have been limited to chloride and various thiolates, including the recently discovered gasotransmitter H$_2$S[9] (LG$^-$=HS$^-$ at pH 7). These LG$^-$ have been chosen to ascertain how quantum yields respond to change in leaving group basicities. Secondly, our focus on the release of thiols anticipates an ultimate goal of developing a photoremovable protecting group for cysteine residues in peptides such as glutathione. Leaving groups such as phenolate or carboxylate are outside the scope of this paper. Moreover, the benzothiophene C-6 carboxylate group greatly complicates their synthesis.

Results

Syntheses

The benzothiophene carboxamides 7-10 (LG$^-$=Cl$^-$) are synthesized by reacting 2-methylaminothioxanthones 13[10] and 14 with acid chlorides 11[11] or 12 (eq. 2).

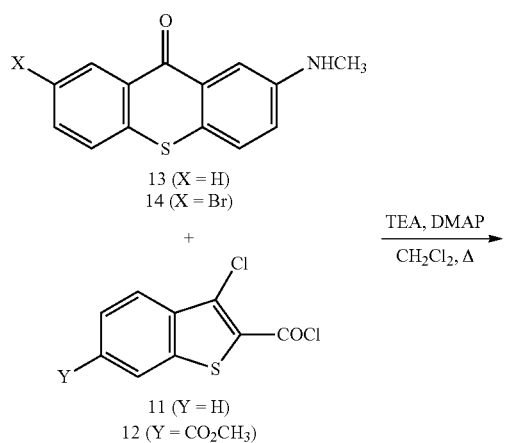

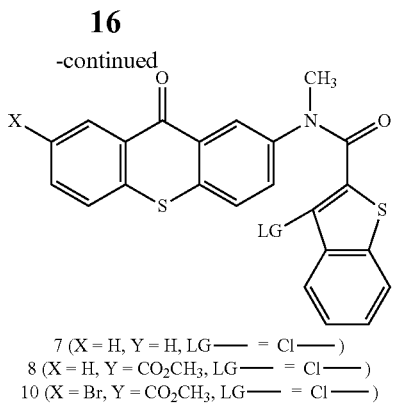

The 3-chloro group of 8 (LG⁻=Cl⁻) is then readily substituted by reaction with thiols[4] to obtain 9 (LG⁻=HS⁻, PhS⁻, PhCH$_2$S⁻) (Scheme 2). The reaction to give acid 9 (LG⁻=PhS⁻) is accompanied by demethylation of the methyl ester, whereas to obtain the acid 9 (LG⁻=PhCH$_2$S⁻, HS⁻), ester hydrolysis was performed prior to introducing the thiolate leaving group.

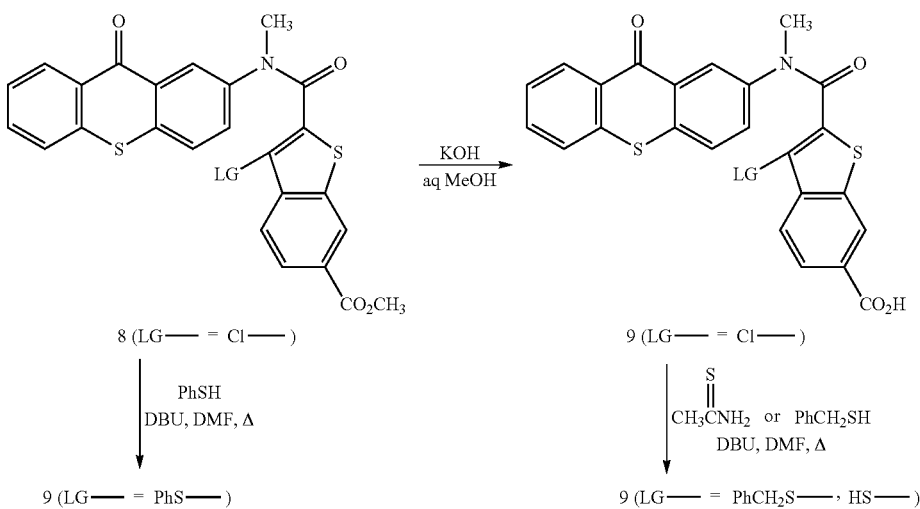

The benzothiophene carbonyl chloride 12 was synthesized from the corresponding cinnamic acid derivative 17 (Scheme 3), whereas the synthesis of benzothiophene 11 (eq. 2) was reported previously.[11]

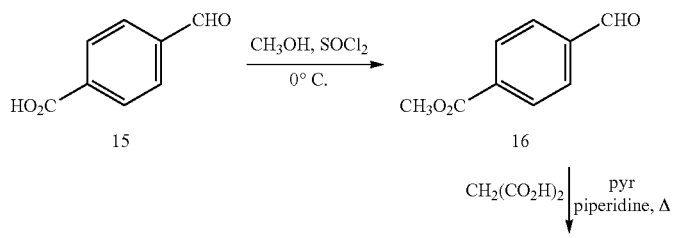

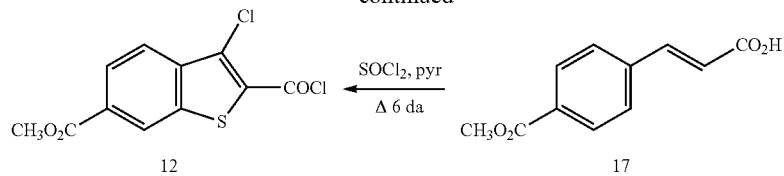

In the case of benzothiophene 12 the precursor, cinnamic acid 17, was obtained by Knoevenagel condensation of 4-formyl methyl benzoate 16.[12] Somewhat unusual reaction conditions were necessary for the esterification step affording 16.

The syntheses of 2-methylaminothioxanthones 13 and 14 (eq 2 and Scheme 4) started with the corresponding known 2-nitro compounds 18[10] and 19[13], which were prepared by literature methods.

Scheme 4

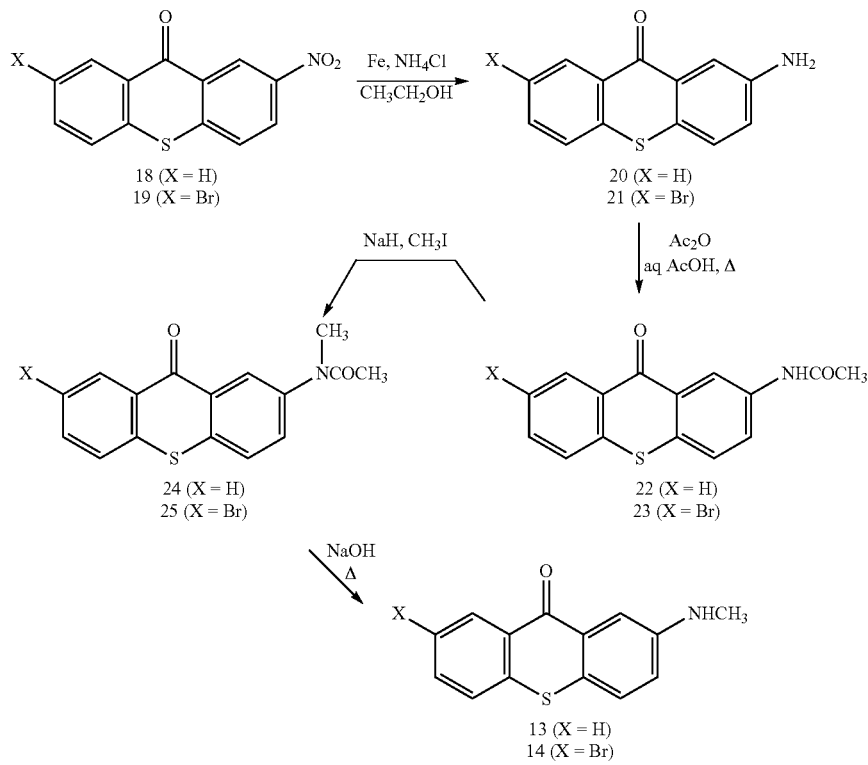

The 2-nitro substituent was reduced to the amines 20 and 21 by iron,[10] followed by acylation. The resultant carboxamides 22 and 23 were then alkylated to introduce the N-methyl substituents 24, 25. Subsequent base hydrolysis of the acetamides furnished the thioxanthone 2-methylamines 13 and 14.

Photochemistry

Figure 2:
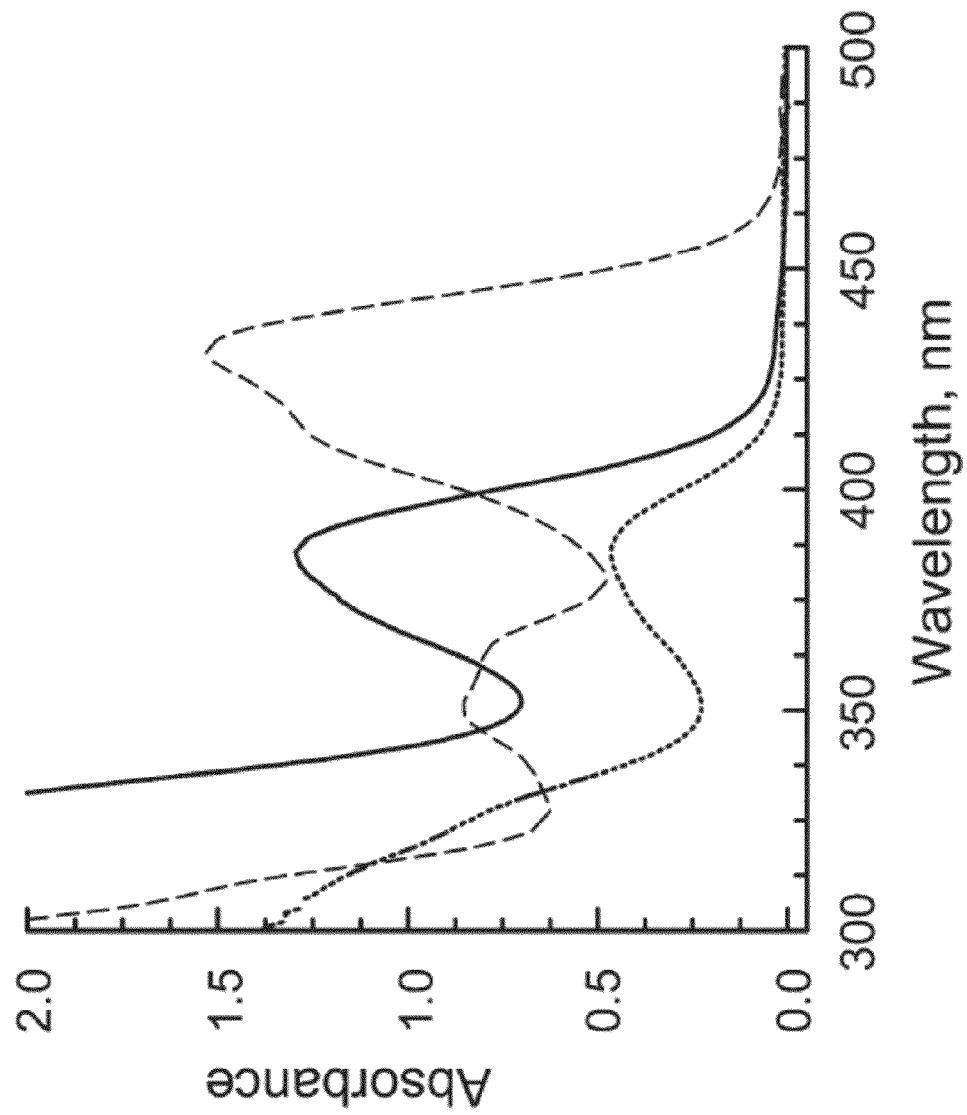
FIG. 2. illustrates the absorption spectra of $2.3\times10^{-4}$ M ester 8 ($LG^-=Cl^-$) (—) in 17% aq phosphate buffer in dioxane, $1.1\times10^{-4}$ M acid 9 ($LG^-=Cl^-$) (...) in 75% aq phosphate buffer in $CH_3CN$, and $1.5\times10^{-4}$ M photoproduct ester 26 produced from ester 8 ($LG^-=Cl^-$) (- - - -).

Ester 8 (LG$^-$=Cl$^-$) and acid 9 (LG$^-$=Cl$^-$) both exhibit absorption maxima at 385 nm in aqueous dioxane or acetonitrile (FIG. 2). For the ester $\epsilon$=5600 M$^{-1}$ cm$^{-1}$, while the acid has $\epsilon$=4200 M$^{-1}$ cm$^{-1}$. For preparative photolyses Pyrex-filtered light from a Hanovia medium pressure mercury lamp was used. A sunlamp was also effective at photolysing all of the compounds in the study. Quantum yields were determined at 390 nm using a monochromator for wavelength selection utilizing a high pressure mercury lamp as the light source.

Preparative photolysis of 10$^{-2}$ M ester 8 (LG$^-$=Cl$^-$) in N$_2$ saturated 19% H$_2$O containing 100 mM phosphate buffer (pH 7) in CH$_3$CN resulted in nearly quantitative expulsion of the chloride leaving group and formation of the single regioisomeric photoproduct 26, as quantified by NMR integration against DMF as an internal standard (Scheme 5).

Scheme 5

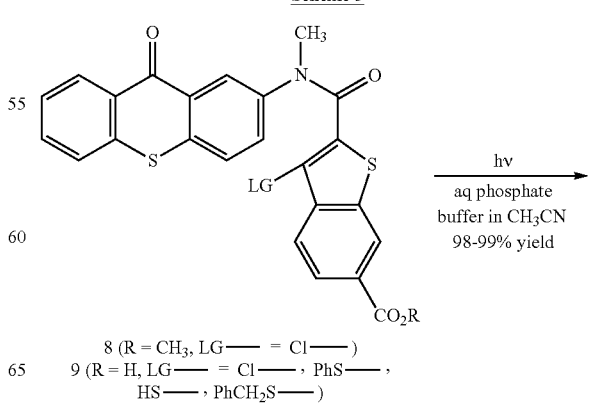

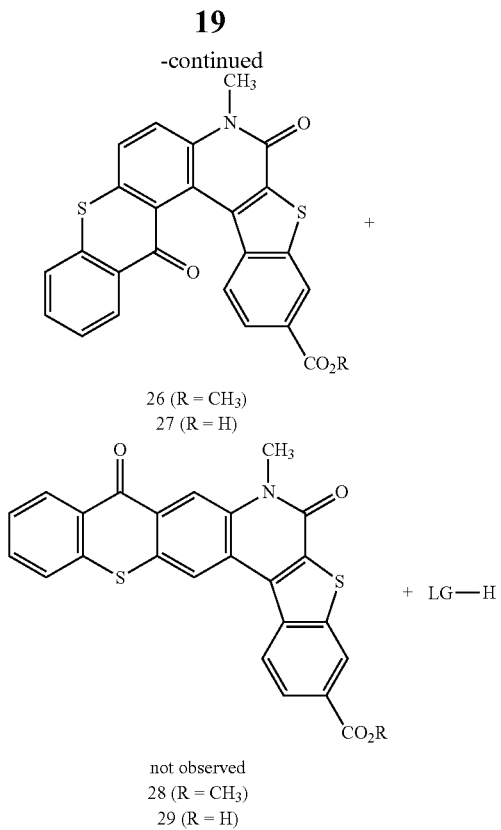

26 (R = CH₃)
27 (R = H)

not observed
28 (R = CH₃)
29 (R = H)

+ LG—H

Photoproduct 26 was identified by ¹H NMR spectroscopy and elemental analysis. The regiospecificity was further established, unambiguously, by 600 MHz ¹H NMR COSY, which clearly showed five vicinal couplings as cross peaks for protons in the three benzenoid rings. Regioisomer 28 would have shown only four vicinal couplings in the COSY spectrum. The solubility of 26 in all solvents was relatively low, which precluded obtaining a satisfactory ¹³C NMR spectrum. The compound was obtainable only as a powder, despite repeated attempts to obtain crystals for structure determination using X-ray diffraction. The absorption spectrum of ester 26 showed a long wavelength maximum at 432 nm ($\epsilon$=10300 $M^{-1}$ $cm^{-1}$) in aq dioxane containing phosphate buffer (FIG. 2).

Similarly, preparative photolysis of 10.2 M acid 9 ($LG^-$=$Cl^-$) in $N_2$ saturated 75% $H_2O$ in $CH_3CN$ containing 100 mM phosphate buffer (pH 7) gave the single regioisomeric photoproduct 27 in 98% yield by NMR integration, as above for 8 ($LG^-$=$Cl^-$). The regiospecificity was again established by 600 MHz ¹H NMR COSY. In addition, the ¹H NMR NOESY showed cross peaks establishing the close spatial proximity of a proton ortho to the thioxanthone carbonyl group and the C-4 and C-5 protons of the benzothiophene benzene ring. The acid photoproduct 27 did not have sufficient solubility in aqueous solvent to obtain the ¹³C NMR spectrum, and since it was only obtainable as a powder, the X-ray structure also could not be determined. Photolysis of acid 9 ($LG^-$=$PhS^-$, $HS^-$, $PhCH_2S^-$) under the same conditions as 8 ($LG^-$=$Cl^-$) also gave photoproduct 27 in 98-100% yields upon expulsion of these thiolate leaving groups. For acid 9 ($LG^-$=$PhCH_2S^-$) the released benzyl thiol was quantified in photolyses of 4.5×10⁻³ M solutions of 35% $D_2O$ in $CD_3CN$ containing phosphate buffer (as above) contained in NMR tubes. Yields were 96% thiol and 99% of 27 at 100% conversion of reactant by ¹H NMR spectroscopy. Very similar results were found when DMSO-$d_6$ was the photolysis solvent.

The photolyses of ester 8 ($LG^-$=$Cl^-$) and acids 9 ($LG^-$= $Cl^-$, $PhS^-$, $HS^-$, $PhCH_2S^-$) were repeated with a 120 W sunlamp for 72 h under otherwise the same conditions described above for the Hanovia runs. In all cases the leaving groups were expelled essentially quantitatively to give exclusively product 26 or 27.

The regiospecific formation of 26 or 27 in the preparative photolyses of ester 8 or acids 9 requires the presence of the ester and carboxylic acid substituents attached to the C-6 position of the benzothiophene ring system of the reactants. In contrast, photolyses of the unsubstituted benzothiophene ring system 7 ($LG^-$=$Cl^-$) in 16% water containing 100 mM phosphate buffer in $CH_3CN$ gave both regioisomeric photoproducts 30 and 31 as a 42:58 mixture, respectively, in 100% yield according to 400 MHz ¹H NMR spectroscopy (Scheme 6).

Scheme 6

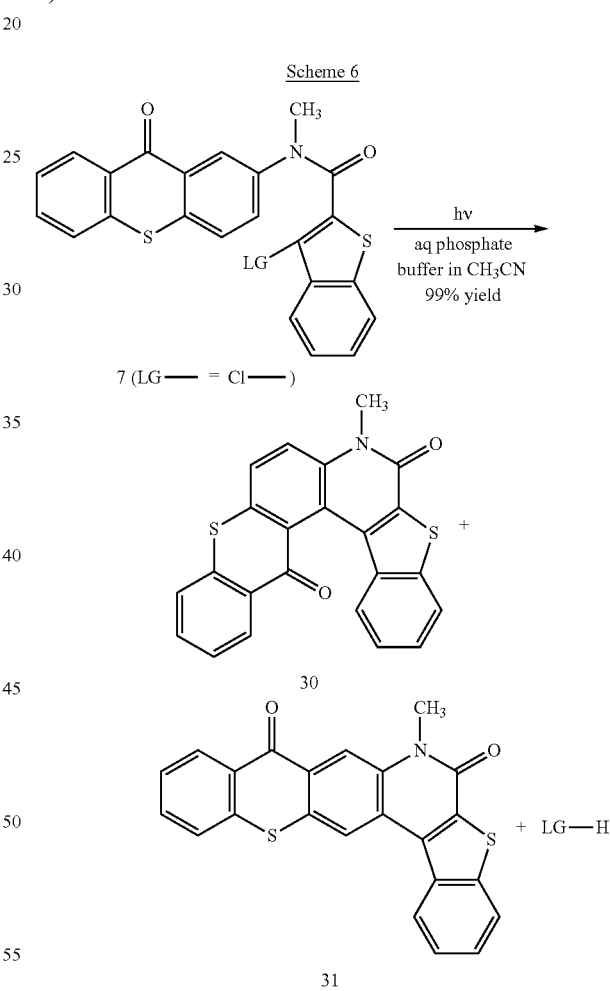

A pure sample of regioisomer 31 crystallized from a DMSO solution of the mixture of 30 and 31. A pure sample of 30 was precipitated upon addition of $H_2O$ to the supernatant. The ¹H NMR spectrum of the pure sample of 31 was distinctly different from that of regioisomer 30. The structure of 30 was assigned by comparing chemical shifts of protons of the N-methyl and the thioxanthone ring system to the corresponding protons of the pure regioisomeric acid 27 (data not shown) that was established by ¹H NMR COSY. Eventually, a crystalline sample of was obtained from CHCl$_3$ as the solvent, and its structure was confirmed by X-ray crystallography.

The product quantum yield for 1.8×10$^{-3}$ M ester 8 (LG$^-$=Cl$^-$) in N$_2$ saturated 19% H$_2$O in dioxane containing 100 mM buffer, photolyses was Φ=0.039, according to NMR spectroscopy using DMF as standard. In addition, the reactant concentration was reduced to 1.0×10$^{-4}$ M, and the quantum yield for photoproduct 26 was found to Φ=0.037. In this latter case the photoproduct was quantified by absorption spectroscopy rather than by NMR spectroscopy. The similar Φ values found for the two reactant concentrations suggest that competitive absorption by photoproduct formed at the front face of the photolysis cell was not significant, possibly because the photolysis wavelength coincided with a minimum in photoproduct absorption (FIG. 2).

Under similar conditions as with 8 (LG$^-$=Cl$^-$), the quantum yield for 7 (LG$^-$=Cl$^-$) was found to be Φ=0.069 for the formation of 30 plus 31, using NMR to quantify the products. The higher observed Φ than ester 8 may be because reactant 7 cyclizes at two sites ortho to the amide nitrogen (C-1 and C-3) of the thioxanthone ring, whereas cyclization of the ester 8 at C-3 is apparently inhibited.

With the more aqueous soluble carboxylic acid 9 the conditions were 2.0×10$^{-3}$ M acid in 75% aq buffer in CH$_3$CN. In N$_2$ saturated aqueous buffer 27 was formed from acid 9 (LG$^-$=Cl$^-$) with Φ=0.034. Quantum yields for the carboxylic acids decreased with increasing basicity of LG$^-$ expelled. Thus, in N$_2$ saturated aqueous buffer and LG$^-$=PhS$^-$, Φ=0.017, whereas for LG$^-$=PhCH$_2$S$^-$, Φ=0.011. However, for LG$^-$=HS$^-$, Φ=0.0079.

In air-saturated solution quantum yields for ester 8 (LG$^-$=Cl$^-$) decreased to Φ=0.019. The significantly lower quantum yield in the presence of air would be consistent with quenching of a triplet excited state by dissolved O$_2$. Furthermore, quenching by 9.2-37×10$^{-6}$ M piperylene as quencher Q gave a slope $k_q\tau$=7.03×10$^4$ M$^{-1}$ for a Stern-Volmer plot Φ°/Φ vs. [Q](data not shown). If it is assumed that $k_q$=ca. 10$^{10}$ M$^{-1}$ s$^{-1}$, then τ would be ca. 7 μs. This lifetime is comparable to 13.3 μs for the unsubstituted thioxanthone in polar protic solvent (methanol) or 6.7 μs in CH$_3$CN.[14]

To determine whether a "heavy atom effect" promoted intersystem crossing of the singlet excited state to the triplet excited state, work focused upon the C-7 bromide of thioxanthone ester 10 (LG$^-$=Cl$^-$). Preparative photolysis of ester 10 in N$_2$ saturated 19% H$_2$O in CH$_3$CN containing 100 mM phosphate buffer (pH 7), as above for ester 8 (LG$^-$=Cl$^-$), exclusively gave regioisomer 32 in 99% yield, and 33 was not observed by $^1$H NMR spectroscopy of the photolysate (Scheme 7).

Scheme 7

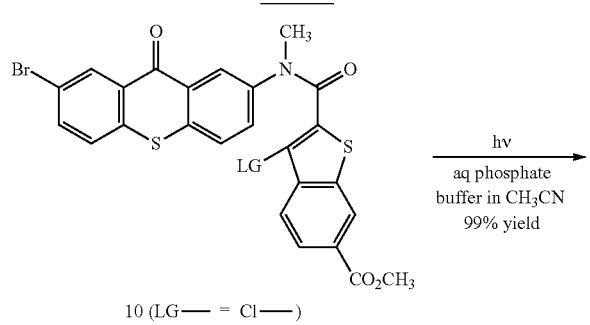

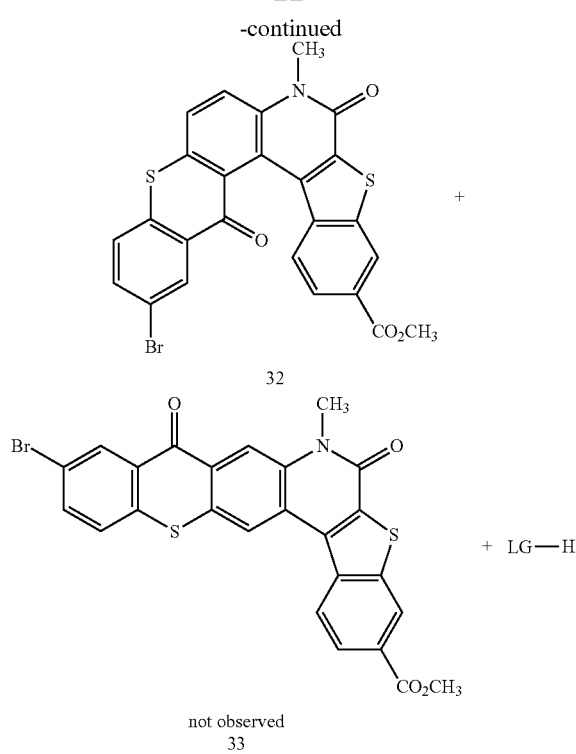

Quantum yield determinations gave Φ=0.053 for formation of 32, which is 38% higher than Φ=0.039 found for ester 8 (LG$^-$=Cl$^-$).

Discussion

The photochemistry of 7-9 is similar to that reported previously for benzothiophene carboxanilides 5.[4] The thioxanthones, however, have the advantage of being photoreactive at relatively long photolysis wavelengths, whereas 5 reacts upon irradiation deep in the UV (310 nm). Photolyses of 7-9 can be conducted at 390 nm or by use of a sunlamp. In both cases the direct photolyses result in expulsion of the various LG$^-$ in nearly quantitative yields, regardless of basicity of the LG$^-$. As with 5, the photochemical mechanism for 7-9 is thought to involve expulsion of a leaving group LG$^-$ from a zwitterionic intermediate 2 (Scheme 1) that is formally produced via excited state 6e electrocyclic ring closure.

By comparison to 7-9, most other commonly used photoremovable protecting groups have longest wavelength maxima at shorter wavelengths: o-nitrobenzyl $\lambda_{max}$ 272 nm (ε=6,200),[15,16] nitroveratryl $\lambda_{max}$ 330 nm (ε=5,000),[16] p-hydroxyphenacyl $\lambda_{max}$ 282 nm (ε=14,000),[17] and desyl $\lambda_{max}$ 323 nm (ε=400).[18] A long wavelength absorber is aminocoumarinylmethyl $\lambda_{max}$ 402 nm (ε=18,600).[19] Likewise, certain brominated hydroxycoumarinylmethyl groups have wavelength maxima ranging from 325-397 nm (ε=ca. 1.2-2.0×10$^4$).[20] Hydroxyquinolinylmethyl protecting groups have maxima at wavelengths as long as 386 nm (ε=3,300).[21] However, the coumarinylmethyl[22] and hydroxyquinolinylmethyl[21] protecting groups only release weakly basic leaving groups. It should be noted that the above wavelength maxima do not represent the practical, usually longer wavelengths used for photorelease experiments.[23] In addition, certain cage compounds, including coumarinylmethyl[20] and hydroxyquinolinylmethyl[21] derivatives undergo uncaging upon 2-photon excitation in the IR region.[24]

Four aspects of the photochemistry of 7-9 and 10 will be discussed further, below. First, quantum yields decrease with increasing leaving group basicity. Secondly, the cyclization step producing the zwitterionic intermediate likely involves the triplet excited state. Quantum yields for 7-10 are generally much lower than for 5, which photolyzes efficiently. Furthermore, the photocyclization products of 7-9 are formed regioselectively or regiospecifically.

For acid 9 the quantum yields for reaction decrease for the series LG⁻=Cl⁻, PhS⁻, and PhCH₂S⁻. This decrease follows the increasing basicities of these anions. As noted, the same trend in Φ was previously reported for 5, although a wider variety of leaving groups was investigated in that case.[4] Nevertheless, as noted previously, the decrease in Φ with increasing LG⁻ basicities is thought to be consistent with the zwitterionic intermediate 2 as undergoing ring opening to regenerate reactant in competition with LG expulsion.

We note that for 9 (LG⁻=HS⁻), the expulsion of HS⁻ is inefficient in terms of Φ, but nevertheless occurs essentially in quantitative chemical yields. The low Φ could be due to quenching of the thioxanthone triplets by the benzothiophene SH moiety. Mercaptans are known quenchers of ketone triplet excited states, and bimolecular rate constants $k_q$ are $10^7$-$10^8$ $M^{-1}$ $s^{-1}$ for quenching of benzophenone triplets.[25] Such quenching has also been noted as being reversible.[25] Such reversibility would be necessary to account for the essentially quantitative yields of photoproduct 27 found upon photolysis of 9 (LG⁻=HS⁻). Given the high yields of 27, we still consider 9 (LG⁻=HS⁻) to be of potential practical use in biological and physiological studies, because the conjugate acid, H₂S, which would be formed upon LG-release at physiological pH, has been found to be involved in regulation of vascular tone and blood pressure, in addition to stimulating natriuresis and diuresis in the kidneys.[26] It has been noted that such studies of the various roles played by H₂S are hindered by the absence of the readily controllable method for its generation.[27]

In the case of ester 8 (LG⁻=Cl⁻) the photoreaction is quenched by both oxygen and piperylene. Such quenching is consistent with the involvement of the triplet excited state in the formation of the proposed zwitterionic intermediate 2. The 38% higher quantum yield observed for the bromo ester 10 (Φ=0.053) as compared to ester 8 (Φ=0.039 may be due to the "heavy atom effect", which is expected to promote intersystem crossing and increase the triplet yield for the bromide. Unsubstituted thioxanthone has a triplet yield of 0.56 in polar, protic solvent (CH₃OH) and 0.85 in nonpolar hydrocarbon solvent (cyclohexane).[28]

Stern-Volmer quenching of the triplet excited state of 8 (LG⁻=Cl⁻) by piperylene yields a triplet excited state lifetime of ca. 7 μs, which is rather like and only somewhat shorter than a typical triplet excited of thioxanthone. The lifetime is consistent with a cyclization step that is not exceptionally rapid. This raises the possibility radiationless decay to the ground state could compete with the cyclization, which would account for relatively low quantum efficiency of Φ=0.037-0.039 for 8 (LG⁻=Cl⁻) as compared to anilide 5 (LG⁻=Cl⁻, Φ=0.23) or p-benzoyl derivative 34 (LG⁻=Cl⁻, Φ=0.15). However, such comparisons are more direct for 7 (LG⁻=Cl⁻), which like 5 or 34, has no carboxylate group at C-6 of the benzothiophene ring. Quantum yields for 7 (LG⁻=Cl⁻) are also rather low at 0.069.

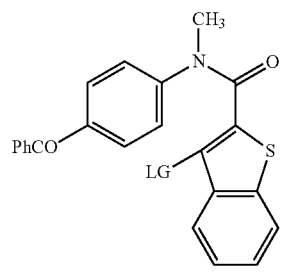

(LG—— = Cl——)

The lower reactivity of thioxanthones vs. 5 or 34 may be due to the fact that $E_T$=64 kcal mol⁻¹ for thioxanthone,[28b] whereas $E_T$=69 kcal mol⁻¹ for unsubstituted benzothiophene.[29] The high quantum yield observed for 5 (LG⁻=Cl⁻) and the progressively lower quantum yields for 34 and the thioxanthones seems to imply that the triplet excited state should be localized on the benzothiophene moiety for the reaction to be efficient. For 5 the triplet excitation is likely localized mainly on the benzothiophene ring. For benzophenone ($E_T$=69 kcal mol⁻¹) the triplet excited state is essentially equienergetic with the benzothiophene. On the other hand, endothermic energy transfer would be needed to populate the benzothiophene triplet excited state upon initial generation of the thioxanthone ($E_T$=64 kcal mol⁻¹) triplet excited state. Energetically less favorable energy transfer from chromophore triplet excited state to the benzothiophene moiety might account for the lower quanatum efficiencies of the thioxanthones relative to 5 and 34.

We performed electronic structure calculations to gain some insight into the mechanism of the photochemical ring closure in an attempt to pinpoint the origins of the different regiospecificity for the carboxyl/methyl ester substituted derivatives 8 and 9. To realistically model the entire photochemical reaction that involves transitions between different electronic states, one would require computationally expensive multi-reference methods and, probably, extensive non-adiabatic dynamics calculations. Here, we adopted a more limited approach and only examined some relevant stationary points on the lowest ground singlet $S_0$ and triplet $T_1$ electronic states using density functional theory (DFT) calculations at the PBE0/6-31G(d) level with solvent effects included using a polarizable continuum model.

Figure 3:
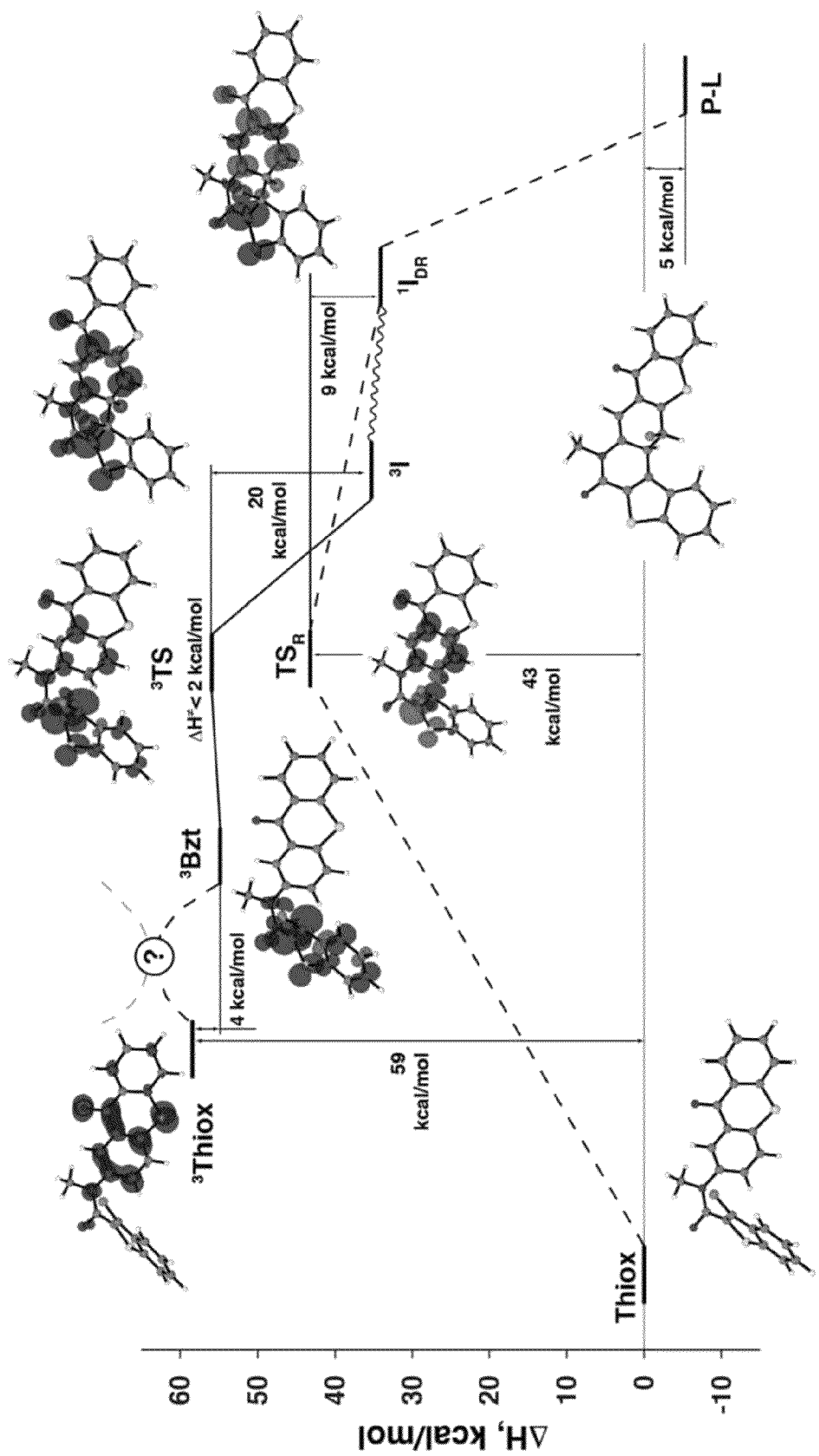
FIG. 3. Illustrates the relative enthalpies of the stationary points on the ground-state singlet $S_0$ and lowest triplet $T_1$ surfaces relevant for formation of the linear ring closure product. Unpaired spin density isosurfaces are shown for open-shell species. The unsubstituted model is shown; relative enthalpies for methyl ester-substituted model are within 1 kcal mol$^{-1}$. All structures correspond to the lowest electronic state of a given multiplicity, as confirmed by wavefunction stability tests.
Figure 4:
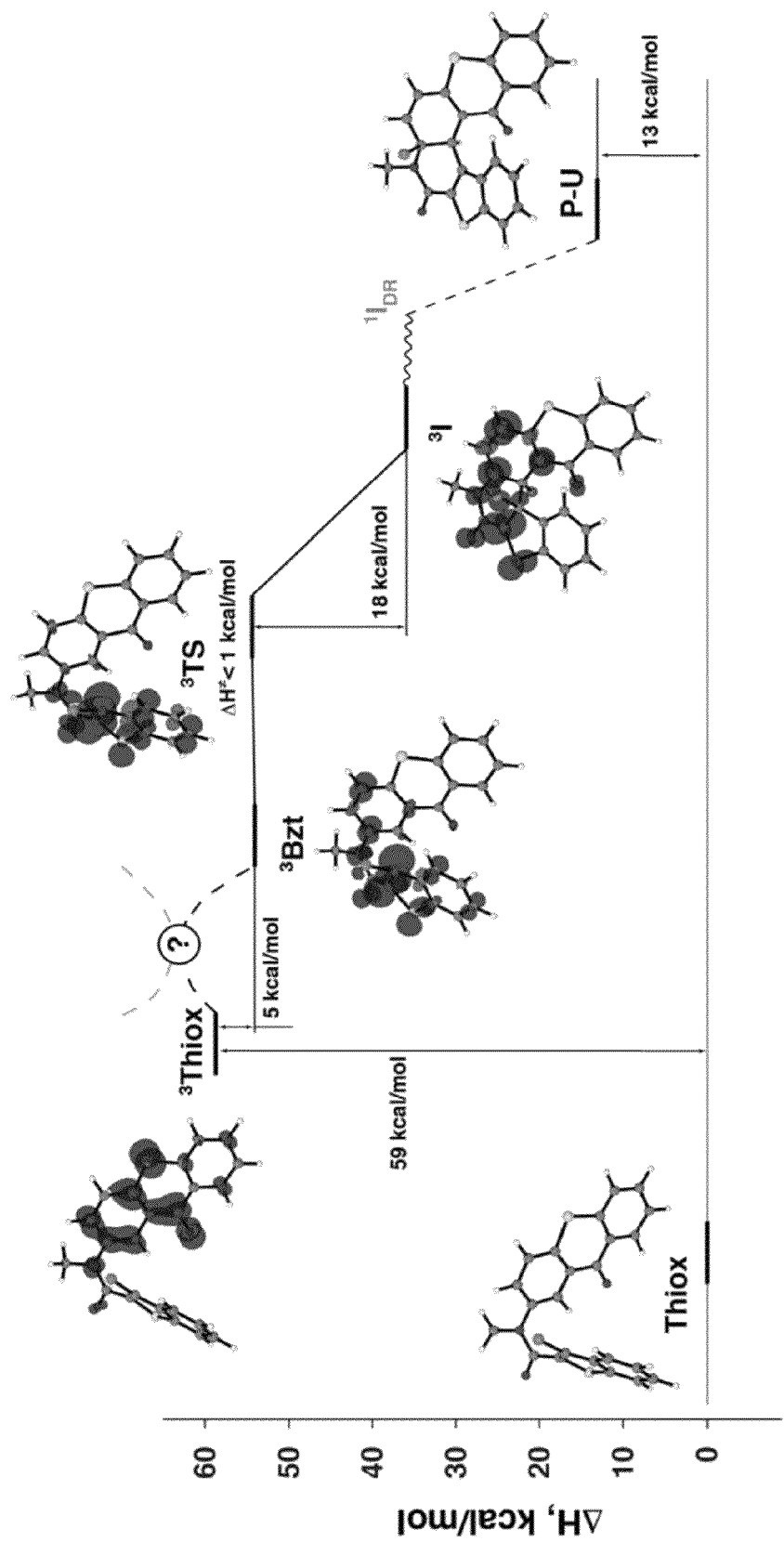
FIG. 4. Illustrates the relative enthalpies of the stationary points on the ground-state singlet $S_0$ and lowest triplet $T_1$ surfaces relevant for the formation of the U-shaped helical ring closure product. Unpaired spin density isosurfaces are shown for open-shell species. The unsubstituted model is shown; the relative enthalpies for methyl ester-substituted model are within 1 kcal mol$^{-1}$. No local minimum corresponds to the $^1I_{DR}$ intermediate, since the geometry optimization directly converges to closed-shell product P-U.

The unsubstituted compound 7 and its methyl ester derivative 8 were considered in two conformations, L (FIG. 3) and U (FIG. 4), that correlate with the corresponding regioisomeric ring closure products, 30 for U and 31 for L in the case of 7, and likewise to products 26 and 28 for U and L conformers in the case of ester 8. For the starting molecules 7 and 8 these conformers are virtually isoenergetic in the ground state, with only with slight preference for the helical conformation U (<0.5 kcal mol⁻¹). Thus, preexcitation conformational dynamics cannot account for the ring closure regiospecificity. FIGS. 3 and 4 depict the stationary points on the ground state singlet and lowest triplet excited state surfaces relevant for formation of the cyclized products of 7. The relative enthalpies for ester compound 8 are within 1 kcal mol⁻¹ and therefore, the Figures are not shown.

We used the ground-state structures for 7 and 8, denoted as Thiox, as starting points to optimize the triplet-state geometries. Relaxed lowest triplet excited state structures ³Thiox are 59 kcal mol⁻¹ higher in enthalpy compared to the $S_0$ state minima. The geometry changes in the ³Thiox excited state are relatively small compared with $S_0$, aside from expected bond length changes. However, further geometry search revealed another minima on the $T_1$ surface ($^3$Bzt) that is 4 kcal mol$^{-1}$ lower relative to the $S_0$-like $^3$Thiox structures. The main geometric difference between $^3$Bzt and $^3$Thiox structures is the pyramidalization at the C-3 carbon atom in $^3$Bzt.

Unpaired spin density plots (FIGS. 3 and 4) show that in $^3$Thiox, which presumably forms from the $S_1$ state via intersystem crossing, the excitation is localized on the thioxanthone moiety. On the other hand, in the pyramidal $^3$Bzt intermediates the excitation is on the benzothiophene moiety. Thus, the $^3$Thiox to $^3$Bzt transformation changes the nature of the lowest adiabatic $T_1$ state and corresponds to excitation transfer between the two parts of the molecule. This transition likely proceeds via a crossing between two diabatic triplet states, corresponding to excited thioxanthone and benzothiophene, respectively. For this transition, C-3 atom pyramidalization appears to be the main reaction coordinate, aside from the solvent coordinate, which also may be important. Modelling of the $^3$Thiox to $^3$Bzt transition would require sophisticated multi-reference calculations; not surprisingly, our attempts to locate a transition state on the lowest adiabatic $T_1$ surface with DFT methods were not successful.

In $^3$Bzt, the pyramidalized C-3 atom is poised to attack the C-3' (L conformer) or the C-1' (U conformer) atoms of the thioxanthone moiety. We located transition state structures $^3$TS (FIGS. 3 and 4) for the ring closure reactions in the $T_1$ state, starting from the $^3$Bzt structures. For the L conformers, the barrier heights are ca. 1-2 kcal mol$^{-1}$ for both 7 and 8. For the U conformers the barrier is virtually non-existent, <1 kcal mol$^{-1}$ for both 7 and 8. The ring closure reaction leads to triplet intermediates $^3$I that are lower in energy than the initial $^3$Bzt structures by 20 and 18 kcal mol$^{-1}$ for the L and U isomers, respectively, for both 7 and 8.

Broken spin symmetry open-shell DFT calculations suggest that the singlet ground state lies just ca. 0.5 kcal mol$^{-1}$ lower than 31 (for the equilibrium 31 geometry) and has a pronounced singlet diradical character ($S^2 \approx 1.0$). Thus, the triplet-to-singlet transition is highly probable once $^3$I is formed, or may even occur during the $^3$Bzt to $^3$I transformation. Geometry optimizations of the singlet diradical intermediates starting from the L-isomers of $^3$I lead to local minima $^1I_{DR}$ (FIG. 3), which are 1 kcal mol$^{-1}$ lower than the corresponding 31 structures and have very similar geometries. Unpaired spin distributions in $^3$I and $^1I_{DR}$ are very similar, with the two unpaired electrons largely uncoupled and spatially separated, as evident from the spin distribution in $^1I_{DR}$. The decoupling between the two unpaired electrons correlates very well with near-degeneracy between the singlet and triplet states for the intermediate I. For the U-isomers, however, geometry optimizations did not locate any minima corresponding to singlet diradical intermediates, $^1ID_R$, as the open-shell character quickly collapses to become closed-shell during the optimization.

The optimized closed-shell singlet structures P-U are 23 kcal mol$^{-1}$ lower than corresponding $^3$I structures and significantly differ in geometry from $^3$I, as the chlorine atom migrates to the C-2' position in structure P-U. We further optimized singlet diradicals $^{11}$DR with a collapsed closed-shell wavefunction. The closed shell species ultimately gives the closed-shell products P-L that are 40 kcal mol$^{-1}$ lower in energy than $^1$I. In the case of P-L the chlorine atom has migrated to the C-4' position.

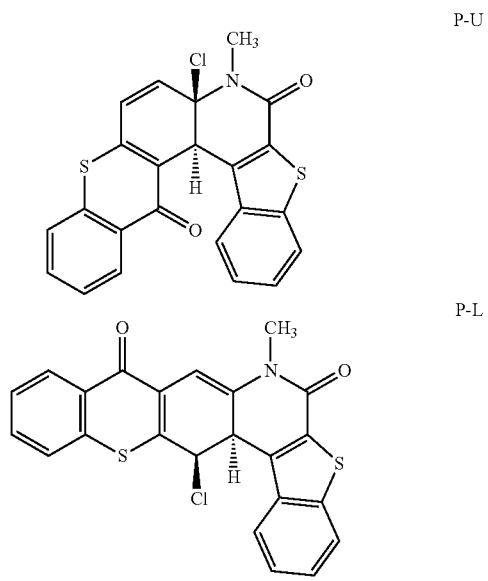

In the case of L isomer, we located an open-shell diradical transition state TS$_R$ that corresponds to the ring reopening in $^1I_{DR}$ leading to the Thiox reactant via a ~10 kcal mol$^{-1}$ barrier (FIG. 3). The diradical intermediates $^1I_{DR}$ correspond to very shallow or, in the case of U isomer, non-existent minima on the potential energy surface. Thus, conversion of $^1I_{DR}$ into products is a more likely process than the reverse ring-opening reaction. In the case of a poorer leaving group, $^1I_{DR}$ can be more stable, which could increase the importance of the ring-opening reaction. Indeed, preliminary DFT calculations for LG$^-$=HO$^-$ substituted models suggest a significantly more stable $^1I_{DR}$ diradical. This agrees well with lower quantum yield previously observed for LG$^-$ that are more basic than LG$^-$=Cl$^-$.

Our DFT calculations (FIGS. 3 and 4) did not find any practically significant differences between the 7 and 8, since the enthalpies calculated, relative to the corresponding Thiox structures, never differed by more than 1 kcal mol$^{-1}$. Moreover, there is no substantial energetic difference between L and U conformers of Thiox, $^3$Thiox, and $^3$Bzt. For both L and U cases the barrier height for the ring closure of $^3$Bzt is extremely low, although the ring closure is slightly more exothermic in the case of the L isomer (20 vs 18 kcal mol$^{-1}$ for L and U, respectively). Further transformations of the ring closure intermediates do differ for L and U isomers, in that L ultimately gives the lower energy product P-L. This is only in agreement with the slight experimental preference for the L isomer product 31 of 7, but is contrary to the regiospecific formation of 26 from 8.

The photoproducts P-L and P-U are not experimentally observed, but they are the calculated products when solvent effects are implicitly included using a polarizable continuum model. Inclusion of discrete water molecules would very likely result in dissociation of the chloride leaving group to give the experimentally observed products involving loss of HCl. Experimentally, we previously observed a product that would be analogous to P-U or P-L. For example, photolysis of 35 gave 36 in CH$_3$CN under nonaqueous conditions, while 37 was the product in aq CH$_3$CN (Scheme 8).[28]

Scheme 8

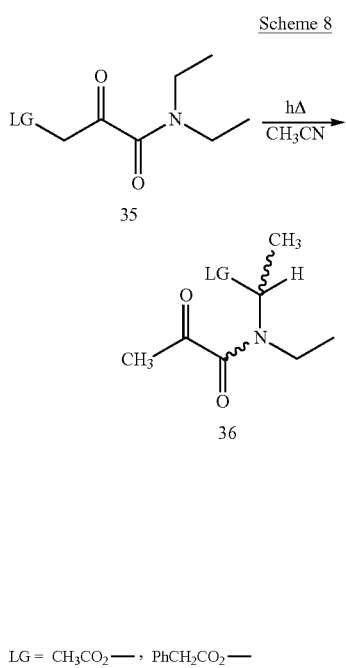

LG = CH₃CO₂—, PhCH₂CO₂—

When water was added to a solution of 36 in CH₃CN, 36 underwent solvolysis to give 37. Our previous study also presented flash photolytic kinetic data in support of a mechanism for formation of 37 involving dissociation of the leaving group from zwitterionic intermediate 38.[28]

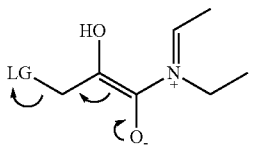

Our view has been that, upon release of the leaving group from 38, the resultant imminium ion undergoes internal return in the ion pair to form 36, while hemiacetal 37 results from capture of the imminium ion by the solvent under aqueous conditions.[30,31] Products P-U and P-L are considered to be closely related to 37, and experimentally, one would also expect them to be quite labile with respect to solvolytic loss of HCl, if they were to be formed.

Calculated enthalpic profiles (FIGS. 3 and 4) suggest that once the pyramidal intermediates ³Bzt are formed, they immediately undergo irreversible ring closure when LG⁻=Cl⁻. Thus, the regiospecificity is likely determined at this or preceding reaction steps. Since L and U conformers are nearly isoenergetic for ³Thiox and ³Bzt (in fact, the U conformer of ³Bzt is 1 kcal mol⁻¹ lower than the L conformer), the unusual regiospecificity of 8 may have its origins in the dynamics of the excitation transfer between the two aromatic systems, ³Thiox to ³Bzt. Careful multi-reference modeling of this rate-limiting step, including calculations of the coupling between the diabatic triplet states involved, are required to test this hypothesis.

Conclusions

Thioxanthones bearing a benzothiophene carboxamide group at the C-2 position are capable of expelling leaving groups such as Cl⁻, PhS⁻, HS⁻ and PhCH₂S⁻ that are originally present at the C-3 position of the benzothiophene ring. The leaving group expulsions can be achieved using 390 nm light or a sunlamp in essentially quantitative yields. Moreover, the inclusion of a carboxylate group at the C-6 position of the benzothiophene ring system greatly improves solubilities in aqueous media. The photorelease of the leaving groups proceeds with quantum yields of 0.01-0.04, depending on leaving basicity. The carboxylate-substituted benzothiophenes photocyclize regiospecifically. The preference is for photoelectrocyclization to the C-1 position of the thioxanthone ring to give a helical photoproduct. C-3 photocyclization is slightly preferred to C-1 photocyclization, when the benzothiophene ring lacks the C-6 carboxylate group. The photocyclizations occur in the triplet excited state according to quenching experiments with known triplet excited state quenchers. DFT calculations show that the triplet excited state cyclization is energetically favourable and produces a triplet excited state. Intersystem crossing of this species produces a singlet diradical, which in water is expected to collapse to the corresponding closed shell species (zwitterion) with C₃—Cl bond breaking to form product.

Experimental

Preparation of 3-chloro-benzo[b]thiophene-2-carboxylic acid methyl-(9-oxo-9H-thioxanthen-2-yl)amide[4] (7) (LG⁻=Cl⁻)

To 1.2 g (5.0 mmol) of 2-methylaminothioxanthen-9-one (13)[10] and 15 mL of triethylamine in 30 mL of anhyd CH₂Cl₂ was added 1.4 g (6.1 mmol) of 3-chlorobenzo[b]thiophene-2-carbonyl chloride (11)[11] dissolved in 10 mL of anhyd CH₂Cl₂ at 5-8° C. in an ice bath. A catalytic amount of DMAP was added. The reaction mixture was warmed to room temperature and stirred for 48 h under N₂. The reaction mixture was filtered to remove triethylamine hydrochloride, the filtrate was washed three times with aq saturated NaHCO₃, H₂O, three times with aq. 2N HCl to remove unreacted amines, H₂O, brine, dried over Na₂SO₄, and concentrated in vacuo to give a dark solid containing amide 7 (LG⁻=Cl⁻). The solid was dissolved in benzene and refluxed with Norite for 2 h, followed by vacuum filtration through Celite to remove colored impurities. The filtrate was concentrated in vacuo and crystallized from benzene to obtain 1.8 g (81% yield) of red crystals, mp 168-170° C. Found: C, 63.14; H, 3.31; N, 3.07%; calcd for C₂₃H₁₄NO₂S₂Cl: C, 63.38; H, 3.21; N, 3.21%; ¹H-NMR (400 MHz, CDCl₃): 3.60 (3H, s), 7.29-7.74 (9H, m), 8.48-8.62 (2H, m); ¹³C-NMR (100 MHz, DMSO-d₆): 38.2, 119.3, 122.5, 123.9, 126.4, 127.0, 127.2, 127.5, 127.6, 128.2, 128.3, 129.2, 129.6, 131.8, 131.9, 133.8, 135.0, 135.9, 136.8, 137.6, 141.7, 162.2, 178.7.

Preparation of 3-chloro-2-[methyl-(9-oxo-9H-thioxanthen-2-yl)-carbamoyl]-benzo[b]thiophene-6-carboxylic acid methyl ester (8) (LG⁻=Cl⁻)

To 1.2 g (5.0 mmol) of 2-methylaminothioxanthen-9-one (13)[10] and 15 mL of triethylamine in 20 mL of anhyd CH₂Cl₂ was added 1.7 g (5.9 mmol) of 3-chloro-2-(chlorocarbonyl)benzo[b]thiophene-6-carboxylic acid methyl ester (12) dissolved in 15 mL of anhyd CH₂Cl₂ at 5-8° C. in an ice bath. A catalytic amount of DMAP was added. The reaction mixture was warmed at room temperature and stirred for 48 h under N₂. The reaction mixture was filtered to remove triethylamine hydrochloride and the filtrate was washed three times with aq saturated NaHCO₃, H₂O, three times with aq. 2N HCl to remove unreacted amines, H₂O, brine, dried over Na₂SO₄, and concentrated in vacuo to give crude product 8. The crude product was chromatographed on silica gel, eluting with 30% ethyl acetate in hexane to give 1.6 g (65% yield) of 8 (LG⁻=Cl⁻), mp 192-193° C., as a yellow powder. Found: C, 61.05; H, 3.28; N, 2.78%; calcd for $C_{25}H_{16}NO_4S_2Cl$: C, 60.79; H, 3.24; N, 2.84%; ¹H-NMR (400 MHz, CDCl₃): 3.61 (3H, s), 3.91 (3H, s), 7.39-7.56 (4H, m), 7.61 (1H, t, J=8.7 Hz), 7.73 (1H, d, J=8.7 Hz), 8.01 (1H, d, J=8.7 Hz), 8.39 (1H, s), 8.52 (1H, s), 8.57 (1H, d, J=8.3 Hz); ¹³C-NMR (100 MHz, CDCl₃): 38.3, 52.6, 120.7, 122.7, 124.9, 126.2, 126.8, 127.2, 127.3, 128.5, 128.7, 129.9, 130.0, 130.7, 132.8, 134.3, 136.6, 136.9, 137.5, 138.7, 141.1, 162.5, 166.5, 179.2.

Preparation of 3-chloro-2-[methyl-(9-oxo-9H-thioxanthen-2-yl)-carbamoyl]-benzo[b]thiophene-6-carboxylic acid (9) (LG⁻=Cl⁻)

To 1.0 g (2.1 mmol) of ester 8 (LG⁻=Cl⁻) in 45 mL MeOH and 15 mL H₂O was added 0.11 g (0.93 equiv) of KOH. The mixture was refluxed for 4 h. After cooling to room temperature, 50 mL of H₂O was added, the solution was washed with ethyl acetate to remove any unreacted ester, and the aq. phase was acidified with conc HCl to pH 2 to give a precipitate. The aqueous suspended precipitate dissolved upon addition of ethyl acetate. The ethyl acetate extract was washed with brine, dried over Na₂SO₄, and concentrated in vacuo to obtain 0.61 g (61% yield) of acid 9 (LG⁻=Cl⁻) as a yellow powder, mp 286-287° C. Found: C, 59.95; H, 3.04; N, 2.93%; calcd for $C_{24}H_{14}NO_4S_2Cl$: C, 60.06; H, 2.92; N, 2.92%; ¹H-NMR (400 MHz, DMSO-d₆): 3.50 (3H, s), 7.39-7.81 (6H, m), 7.88 (1H, d, J=8.5 Hz), 8.30 (1H, d, J=7.8 Hz), 8.34 (1H, s), 8.58 (1H, s), 13.16 (1H, br); ¹³C-NMR (100 MHz, DMSO-d₆): 38.1, 118.9, 122.4, 125.7, 126.6, 127.1, 127.3, 127.9, 128.1, 129.0, 129.4, 129.5, 131.6, 133.4, 135.3, 135.8, 136.6, 137.4, 137.8, 141.3, 161.6, 167.1, 178.5.

Preparation of 2-[methyl-(9-oxo-9H-thioxanthen-2-yl)-carbamoyl]-3-phenylsulfanyl-benzo[b]thiophene-6-carboxylic acid (9) (LG⁻=PhS⁻)[4]

To a solution of 1.03 g (2.1 mmol) of ester 8 (LG⁻=Cl⁻) in 10 mL DMF was added 0.43 mL (0.46 g, 4.2 mmol) of thiophenol, followed by 0.63 mL, (0.64 g, 4.2 mmol) of DBU. The reaction mixture was stirred for 72 h at 80° C. under N₂ and then 50 mL of ethyl acetate was added. The ethyl acetate solution was washed with aq 1N HCl (250 mL) to remove excess of DBU and then washed three times with aq 1N NaOH (100 mL). The combined aqueous base solution was acidified with conc. HCl (pH=2). The resultant light yellow precipitate was collected by filtration and crystallized from MeOH, followed by drying under vacuum, to obtain 0.90 g (78% yield) of acid 9 (LG⁻=PhS⁻) as a yellow powder, mp 278-279° C. Found: C, 64.94; H, 3.44; N, 2.48%; calcd for $C_{30}H_{19}NO_4S_3$: C, 65.1; H, 3.44; N, 2.53; ¹H-NMR (400 MHz, DMSO-d₆) 3.48 (3H, s), 6.63-7.12 (5H, m), 7.29-8.21 (7H, m), 8.21-8.41 (2H, m), 8.66 (1H, s), 13.1 (1H, s); ¹³C-NMR (100 MHz, DMSO-d₆): 38.1, 121.5, 123.8, 126.0, 126.6, 126.7, 127.3, 127.4, 127.7, 128.2, 128.5, 129.2, 129.4, 129.6, 129.7, 132.0, 133.8, 134.8, 135.9, 136.9, 139.3, 141.1, 141.5, 146.5, 162.9, 167.4, 178.6.

Preparation of 3-benzylsulfanyl-2-[methyl-(9-oxo-9H-thioxanthen-2-yl)-carbamoyl]-benzo[b]thiophene-6-carboxylic acid (9) (LG⁻=PhCH₂S⁻)[4]

To a solution of 1.0 g (2.1 mmol) of acid 9 (LG⁻=Cl⁻) in 10 mL DMF was added 0.75 mL (0.78 g, 6.3 mmol) of benzyl mercaptan followed by 1.2 mL (1.3 g, 8.4 mmol) of DBU. The reaction mixture was stirred for 48 h at 80° C. under N₂. The volatiles including DBU and benzyl mercaptan were evaporated at 80° C. under vacuum for 6 h without air contact. The residue was dissolved in CHCl₃, filtered, and the filtrate was washed three times with H₂O, brine and concentrated in vacuo to obtain crude acid 9 (LG⁻=PhCH₂S⁻) as light yellow solid. The crude acid was dissolved in 17% H₂O in CH₃CN containing 100 mM phosphate buffer at pH 7 and filtered. The filtrate was acidified with conc. HCl, to obtain a precipitate, which was collected by filtration. Repeating this purification procedure gave 0.83 g (70% yield) of acid 9 (LG⁻=PhCH₂S⁻) as a light yellow powder, mp 151-152° C. Found: C, 65.60; H, 3.75; N, 2.49%; calcd for $C_{31}H_{21}NO_4S_3$: C, 65.61; H, 3.70%; N, 2.47%; ¹H-NMR (400 MHz, CDCl₃): 3.57 (3H, s), 4.03 (2H, s), 7.04-7.67 (6H, m), 7.86 (1H, s), 8.41 (1H, s), 8.51-8.59 (2H, m); ¹³C-NMR (100 MHz, CDCl₃): 38.4, 41.2, 124.0, 125.5, 126.0, 126.2, 126.7, 126.8, 127.1, 127.5, 128.6, 128.8, 129.2, 129.9, 130.1, 131.0, 132.8, 136.5, 137.0, 137.6, 138.6, 141.3, 143.7, 145.3, 163.9, 171.2.179.4.

Preparation of 3-mercapto-2-[methyl-(9-oxo-9H-thioxanthen-2-yl)-carbamoyl]-benzo[b]thiophene-6-carboxylic acid (9) (LG⁻=HS⁻)

To a solution of 0.29 g (0.61 mmol) of acid 9 (LG⁻=Cl⁻) in 10 mL DMF was added 0.14 g (1.8 mmol) of thioacetamide followed by 0.27 mL (0.27 g, 1.8 mmol) of DBU. The reaction mixture was stirred for 72 h at 100° C. under N₂. To the reaction mixture was added 50 mL ethyl acetate and 100 mL of H₂O. The aq. layer was separated and extracted with ethyl acetate and then acidified with conc. HCl (pH=2) to obtain 0.15 g of a precipitate upon filtration. Most of the light yellow precipitate was then dissolved in 15 mg of KOH in 50 mL of H₂O and filtered. The filtrate was acidified with 1 N HCl and the precipitate was obtained by filtration. The precipitate was dried under vacuum and crystallized from ethyl acetate to give 0.12 g (42% yield) of NMR pure compound (9) (LG⁻=HS⁻), mp 210-212° C. Found: C, 60.61; H, 3.48; N, 2.69%; calcd for $C_{24}H_{15}NO_4S_3$: C, 60.38; H, 3.14; N, 2.94%; ¹H-NMR (400 MHz, DMSO-d₆): 3.20 (3H, s), 7.24-7.51 (3H, m), 7.55-7.71 (4H, m), 8.24-8.31 (2H, m), 8.50 (1H, s); ¹³C-NMR (100 MHz, DMSO-d₆): 38.1, 123.4, 124.8, 125.5, 125.9, 126.6, 126.9, 127.3, 127.7, 128.3, 128.9, 129.1, 129.5, 131.4, 133.5, 135.5, 136.6, 138.7, 141.0, 141.3, 146.5, 162.0, 167.0, 178.5.

Preparation of 2-[(7-bromo-9-oxo-9H-thioxanthen-2-yl)-methyl-carbamoyl]-3-chloro-benzo[b]thiophene-6-carboxylic acid methyl ester (10) (LG⁻=Cl⁻)

To 0.51 g (1.6 mmol) of 2-bromo-7-methylamino-thioxanthen-9-one (14) and 10 mL of triethylamine in 15 mL of anhyd CH₂Cl₂ was added 0.61 g (2.1 mmol) of 3-chloro-2-chlorocarbonyl-benzo[b]thiophene-6-carboxylic acid methyl ester (12) dissolved in 10 mL of anhyd CH₂Cl₂ at 5-8° C. in an ice bath. A catalytic amount of DMAP was added. The reaction mixture was warmed at room temperature and stirred for 48 h under N₂. The reaction mixture was filtered to remove triethylamine hydrochloride salt, the filtrate was washed three times with aq saturated NaHCO₃, H₂O, three times with aq. 2N HCl to remove unreacted amines, H₂O, brine, dried over Na₂SO₄, and concentrated in vacuo to give crude ester 10. The crude ester 10 was chromatographed on silica gel, eluting with 20% ethyl acetate in hexane to give 0.55 g (60% yield) of NMR pure 10 (LG⁻=Cl⁻) as a brown powder, mp 237-239° C. Found: C, 52.09; H, 2.64; N, 2.47%; calcd for $C_{25}H_{15}NO_4S_2ClBr$: C, 52.40; H, 2.62; N, 2.44%; $^1$H-NMR (400 MHz, CDCl$_3$): 3.61 (3H, s), 3.92 (3H, s), 7.35-7.54 (3H, m), 7.66-7.80 (2H, m), 8.02 (1H, d, J=8.2 Hz), 8.40 (1H, s), 8.51 (1H, s), 8.69 (1H, s); $^{13}$C-NMR (100 MHz, CDCl$_3$): 38.3, 52.6, 120.8, 120.9, 122.8, 124.9, 126.3, 127.3, 127.4, 127.8, 128.6, 129.6, 130.0, 131.0, 132.7, 134.1, 135.8, 136.1, 137.6, 138.7, 141.4, 162.5, 166.5, 178.1.

Preparation of 3-chloro-2-chlorocarbonyl-benzo[b]thiophene-6-carboxylic acid methyl ester (12)

A stirred solution of 10.0 g (0.048 mol) of (E)-4-(methoxycarbonyl)cinnamic acid (17)[12] and 0.8 mL pyridine in 52 mL (0.72 mol) of thionyl chloride was refluxed for 6 days. After cooling at room temperature, 100 mL of 2N HCl was added until pH 2 was obtained and the mixture was filtered. The solid crude acid was dried under vacuum. To the crude acid in 50 mL benzene was added, dropwise, 5.7 g (0.048 mol, 3.5 mL) of thionyl chloride under N$_2$. The reaction mixture was refluxed overnight and then concentrated in vacuo to give 6.9 g (51% yield) of acid chloride 12 as a colorless powder, mp 259-260° C. $^1$H-NMR (400 MHz, DMSO-d$_6$): 3.87 (3H, s), 7.91 (1H, d, J=8.7 Hz), 8.01 (1H, d, J=8.7 Hz), 8.53 (1H, s).

Preparation of 2-methylaminothioxanthen-9-one (13)

A mixture of 0.99 g (3.5 mmol) of amide 24 and 100 mL of aqueous 2 M NaOH was refluxed for 12 h. Upon cooling the reaction mixture was acidified with concentrated HCl to pH=1 and then extracted with CH$_2$Cl$_2$. The extract was dried over Na$_2$SO$_4$ and concentrated in vacuo to give 0.47 g (56% yield) of amino ketone 13 as a yellow powder, mp 172-175° C. $^1$H-NMR (400 MHz, CDCl$_3$): 2.95 (3H, s), 3.98 (1H, br), 6.98 (1H, d, J=8.7 Hz), 7.36-7.48 (2H, m), 7.53-7.60 (2H, m), 7.77 (1H, s), 8.62 (1H, d, J=8.1 Hz).

Preparation of 2-bromo-7-methylaminothioxanthen-9-one (14)

A mixture of 1.13 g (3.1 mmol) of amide 25 and 100 mL of aqueous 2 M NaOH was refluxed for 12 h. Upon cooling the reaction mixture was acidified with concentrated HCl to pH=1 and then extracted with CH$_2$Cl$_2$. The extract was dried over Na$_2$SO$_4$, and concentrated in vacuo to give 0.36 g (36% yield) of amino ketone 14 as red powder, mp 198-200° C. $^1$H-NMR (400 MHz, CDCl$_3$): 2.95 (3H, s), 4.02 (1H, br), 6.98 (1H, d, J=8.6 Hz), 7.38 (1H, d, J=8.6 Hz), 7.43 (1H, d, J=8.6 Hz), 7.66 (1H, d, J=8.6 Hz), 7.73 (1H, s), 8.74 (1H, s).

Preparation of 2-amino-7-bromo-thioxanthen-9-one (21)[10]

A mixture of 1.7 g (5.0 mmol) of 2-bromo-7-nitrothioxanthen-9-one (19)[13], 1.6 g (31 mmol) ammonium chloride, and 0.90 g (16 mmol) iron in 60 mL water and 200 mL ethanol was refluxed overnight. After hot vacuum filtration through silica gel, the silica gel was washed with 30 mL and combined with the filtrate. The combined filtrate was concentrated in vacuo. To the residue was added 150 mL chloroform. The chloroform solution was dried over anhydrous sodium sulfate and concentrated in vacuo to give 1.0 g (66% yield) of NMR pure 21 as a brown powder, mp 201-203° C. $^1$H-NMR (400 MHz, CDCl$_3$): 3.96 (2H, br), 7.04 (1H, d, J=8.9 Hz), 7.39 (1H, d, J=8.9 Hz), 7.43 (1H, d, J=8.9 Hz), 7.66 (1H, d, J=8.3 Hz), 7.86 (1H, s), 8.72 (1H, s).

Preparation of N-(7-bromo-9-oxo-9H-thioxanthen-2-yl)-acetamide (23)

A mixture of 1.0 g (3.3 mmol) amino ketone 21, 50 mL glacial acetic acid, and 11.6 g (114 mmol) of acetic anhydride was stirred for overnight at room temperature. After adding 100 mL water with stirring, the resultant precipitate was filtered, washed with four times with 50 mL H$_2$O, and 10 mL of MeOH. The precipitate was washed with CHCl$_3$ and dried under vacuum to give 1.1 g (95% yield) of NMR pure acetamide derivative 23 as brown powder, mp 219-222° C. $^1$H-NMR (400 MHz, DMSO-d$_6$): 2.08 (3H, s), 7.78 (1H, d, J=8.6 Hz), 7.81 (1H, d, J=8.6 Hz), 7.90 (1H, d, J=9.4 Hz), 8.01 (1H, d, J=9.4 Hz), 8.48 (1H, s), 8.67 (1H, s), 10.34 (1H, s).

Preparation of N-methyl-N-(9-oxo-9H-thioxanthen-2-yl)-acetamide (24)

To a stirred solution of 1.2 g (4.5 mmol) of N-(9-oxo-9H-thioxanthen-2-yl)-acetamide[10] 22 in 20 mL of THF was added 0.23 g (5.8 mmol) of NaH (60%) under N$_2$. The mixture was stirred for 15 min followed by dropwise addition of 0.96 g (6.8 mmol) of methyl iodide. The reaction mixture was stirred at room temperature for 48 h and then concentrated in vacuo to obtain a crude solid residue. To the residue was added CHCl$_3$, followed by filtration and concentration of the filtrate in vacuo to obtain 1.1 g (80% yield) of methyl amide 24 as a yellow powder, mp 246-248° C. $^1$H-NMR (400 MHz, CDCl$_3$): 1.92 (3H, s), 3.33 (3H, s), 7.41-7.74 (5H, m), 8.44 (1H, s), 8.62 (1H, d, J=8.5 Hz).

Preparation of N-(7-bromo-9-oxo-9H-thioxanthen-2-yl)-N-methyl-acetamide (25)

To a stirred solution of 1.1 g (3.2 mmol) acetamide 23 in 20 mL of THF was added 0.17 g (4.2 mmol) of NaH (60%) under N$_2$. The mixture was stirred for 15 min followed by the dropwise addition of 0.70 g (4.9 mmol) of methyl iodide. The reaction mixture was stirred at room temperature for 48 h and then concentrated in vacuo to obtain a solid residue. To the residue was added CHCl$_3$, followed by filtration and concentration of the filtrate in vacuo to obtain 1.1 g (97% yield) of methyl amide (25) as a yellow solid, mp 240-241° C. $^1$H-NMR (400 MHz, CDCl$_3$): 1.93 (3H, s), 3.34 (3H, s), 7.46-7.54 (2H, m), 7.66 (1H, d, J=8.7 Hz), 7.76 (1H, d, J=8.7 Hz), 8.45 (1H, s), 8.75 (1H, s).

Preparation of 6-methylcarboxylate-[1]benzothiopheno[2,3-c]benzo[a]anthracene-4-methyl-4H-7-thia-4-aza-3,12-dione (26) by photolysis of 8 (LG$^-$=Cl$^-$)

A 0.010 M solution of 8 (LG$^-$=Cl$^-$) in N$_2$ saturated 17% H$_2$O in CH$_3$CN containing 100 mM phosphate buffer at pH 7 was irradiated with a 450 W Hanovia medium pressure mercury lamp with a Pyrex filter for 90 min. The photoproduct was isolated by filtration. The photoproduct was washed with H$_2$O and a small amount of CHCl$_3$ and dried under vacuum. The product was a yellow powder, mp >300° C. Found: C, 65.39; H, 3.40; N, 3.11%; calcd for $C_{25}H_{15}NO_4S_2$: C, 65.65; H, 3.28; N, 3.06%; $^1$H-NMR (400 MHz, DMSO-d$_6$): 3.89 (3H, s), 3.91 (3H, s), 7.71 (1H, d, J=8.7 Hz), 7.72 (1H, t, J=7.0 Hz), 7.85 (1H, d, J=8.1 Hz), 7.86 (1H, t, J=7.0 Hz), 7.97 (1H, d, J=8.1 Hz), 8.08 (1H, d, J=8.7 Hz), 8.13 (1H, d, J=7.8 Hz), 8.16 (1H, d, J=8.7 Hz), 8.85 (1H, s); The $^1$C-NMR could not be obtained due to low solubility in $d_6$-DMSO. A COSY spectrum in $d_6$-DMSO was obtained (see Supporting Information).

Preparation of [1]benzothiopheno-6-carboxylic acid [2,3-c]benzo[a]anthracene-10-bromo-4-methyl-4H-7-thia-4-aza-3,12-dione (27) by photolysis of 9 (LG$^-$=Cl$^-$)

A 0.010 M solution of 13 (LG$^-$=Cl$^-$) in $N_2$ saturated 75% $H_2O$ in $CH_3CN$ containing 100 mM phosphate buffer at pH 7 was irradiated with a 450 W Hanovia medium pressure mercury lamp with Pyrex filter for 90 min. The photolysate was acidified to pH 2 with conc. HCl to precipitate the photoproduct carboxylic acid 27. The photoproduct was obtained by filtration, washing with $H_2O$, and drying under vacuum, as a yellow powder, mp >300° C. Found: C, 64.66; H, 3.03; N, 3.10; calcd for $C_{24}H_{13}NO_4S_2$: C, 65.01; H, 2.93; N, 3.16%; $^1$H-NMR (400 MHz, DMSO-$d_6$): 3.87 (3H, s), 7.66 (1H, d, J=8.6 Hz), 7.71 (1H, t, J=7.9 Hz), 7.82 (1H, d, J=9.2 Hz), 7.84 (1H, t, J=7.9 Hz), 7.95 (1H, d, J=7.9 Hz), 8.06 (1H, d, J=9.2 Hz), 8.12 (1H, d, J=9.2 Hz), 8.14 (1H, d, J=9.2 Hz), 8.77 (1H, s); $^1$H NMR COSY and $^1$H NMR NOESY were obtained (see Supporting Information); $^{13}$C-NMR (100 MHz, DMSO-$d_6$) was not obtained due to low solubility.

Preparation of [1]benzothieno[2,3-c]benzo[a]anthracene-4-methyl-4H-7-thia-4-aza-3,12-dione (30) and its regioisomer 31 by photolysis of 7 (LG$^-$=Cl$^-$)

A 0.010 M solution of 7 (LG$^-$=Cl$^-$) in $N_2$ saturated 17% $H_2O$ in $CH_3CN$ containing 100 mM phosphate buffer at pH 7 was irradiated with a 450 W Hanovia medium pressure mercury lamp with a Pyrex filter for 90 min. The photoproduct was isolated by filtration as a mixture of two isomers, 30, 31. The mixture of product isomers was dissolved in hot DMSO. Solid photoproduct isomer 31 was obtained upon cooling of the hot DMSO and filtration. Photoproduct isomer 31 was washed with water and methanol and dried under vacuum to obtain 31 as floppy powder, mp >300° C. Solid photoproduct isomer 30 was obtained upon addition of water to the above DMSO filtrate by filtration, after washing with water and methanol. The photoproduct isomer 30 was crystallized from $CHCl_3$ to give a yellow crystalline solid, mp 271-273° C.

The photoproduct isomer 30 was characterized. Found: C, 68.88; H, 3.46; N, 3.35%; calcd for $C_{23}H_{13}NO_2S_2$: C, 69.17; H, 3.26; N, 3.51%; $^1$H-NMR (400 MHz, DMSO-$d_6$): 3.87 (3H, s), 7.33 (1H, t, J=7.8 Hz), 7.54 (1H, t, J=8.0 Hz), 7.57 (1H, d, J=8.7 Hz), 7.67 (1H, t, J=8.1 Hz), 7.84 (1H, t, J=8.1 Hz), 7.95 (1H, d, J=8.1 Hz), 8.01 (1H, d, J=9.4 Hz), 8.09 (1H, d, J=6.7 Hz), 8.12 (1H, d, J=8.1 Hz), 8.19 (1H, d, J=8.1 Hz); $^{13}$C-NMR (100 MHz, DMSO-$d_6$): 30.7, 115.9, 121.8, 124.2, 124.5, 125.8, 126.6, 127.2, 127.7, 127.8, 128.0, 129.4, 131.7, 132.5, 133.2, 133.9, 135.8, 136.2, 136.4, 138.7, 140.9, 157.8, 181.8.

The photoproduct isomer 31 was characterized. Found: C, 69.19; H, 3.36; N, 3.59%; calcd for $C_{23}H_{13}NO_2S_2$: C, 69.17; H, 3.26; N, 3.51%; $^1$H-NMR (400 MHz, DMSO-$d_6$): 3.78 (3H, s), 7.46 (1H, t, J=7.1), 7.55-7.69 (4H, m), 8.13 (1H, d, J=7.1 Hz), 8.34 (1H, d, J=8.4 Hz), 8.38 (1H, s), 8.79 (1H, s), 8.85 (1H, d, J=4.5 Hz); The $^{13}$C-NMR (100 MHz, DMSO-$d_6$) could not be obtained due to low solubility.

Preparation of 6-methylcarboxylate-[1]benzothiopheno[2,3-c]benzo[a]anthracene-10-bromo-4-methyl-4H-7-thia-4-aza-3,12-dione (32) by photolysis of (10) (LG$^-$=Cl$^-$)

A 25 mL solution comprised of 0.010 M of 10 (LG$^-$=Cl$^-$) in $N_2$ saturated 20% $H_2O$ in $CH_3CN$ containing 100 mM phosphate buffer at pH 7 was irradiated with a 450 W Hanovia medium pressure mercury lamp with Pyrex filter for 60 min. The photoproduct was isolated by filtration and washed with $H_2O$, washed with a small amount of $CHCl_3$, and dried under vacuum. Photoproduct 32 was a yellow powder, mp >300° C. Found: C, 55.69; H, 2.72; N, 2.53%; calcd for $C_{25}H_{14}NO_4S_2Br$: C, 55.97; H, 2.61; N, 2.61%; $^1$H-NMR (400 MHz, DMSO-$d_6$): 3.87 (3H, s), 3.92 (3H, s), 7.66 (1H, d, J=8.7 Hz), 7.83 (1H, d, J=8.7 Hz), 7.93 (1H, d, J=8.7 Hz), 7.99 (1H, d, J=8.7 Hz), 8.05 (1H, d, J=8.7 Hz), 8.14 (1H, s), 8.16 (1H, d, J=8.7 Hz), 8.80 (1H, s); The $^{13}$C-NMR (100 MHz, DMSO-$d_6$) could not be obtained due to low solubility.

General Procedure for Product Quantum Yield Determinations.

A semi-micro optical bench was used for quantum yield determinations, similar to the apparatus described by Zimmerman.[32] Light from a 200 W high-pressure mercury lamp was passed through an Oriel monochromator, which was set to 390 nm wavelengths. The light was collimated through a lens. A fraction of the light was diverted 90° by a beam splitter to a 10×3.6 cm side quartz cylindrical cell containing an actinometer. The photolysate was contained in a 10×1.8 cm quartz cylindrical cell of 25 mL volume. The concentrations of the reactants were 0.0018-0.0030 M. All quantum yields reported herein were the average of two or more independent runs. Behind the photolysate was mounted a quartz cylindrical cell containing 25 mL of actinometer. Light output was monitored by ferrioxalate actinometery using the splitting ratio technique.

For 7 (LG$^-$=Cl$^-$), 8 (LG$^-$=Cl$^-$), and 10 (LG$^-$=Cl$^-$) 50 mL of water was added to the photolysate, and the diluted photolysate was extracted four times with 30 mL of $CH_2Cl_2$. The combined extracts were washed twice with 30 mL water, brine, and concentrated in vacuo. The residue was dissolved in $d_6$-DMSO. DMF was added as a standard for NMR analyses (vide infra). However, for 7 (LG$^-$=Cl$^-$) the NMR solvent was $CDCl_3$ and the NMR standard was DMSO.

For 9 (LG$^-$=Cl$^-$, PhS$^-$, HS$^-$, PhCH$_2$S$^-$) the photolysate was adjusted to pH 2 by addition of 3 N HCl. The resultant precipitate was collected by suction filtration and washed with 50 mL water. The precipitate was transferred to a flask, and any untransferred precipitate was dissolved in DMSO and combined with the transferred precipitate. The DMSO was evaporated to dryness under vacuum and DMSO-$d_6$ was added along with DMF as a standard for NMR analysis.

Products were analyzed by $^1$H NMR spectroscopy using DMF or DMSO as the internal standard and conversions were 12-16%. At the concentrations used most of the incident light would have been absorbed near the front face of the photolysis cell, raising the concern that the photoproducts formed during the photolyses could competitively absorb the incident light, reducing the light absorbed by the reactants. This internal filter effect would depress the observed $\Phi$ values below the actual values. In the case of 8 (LG$^-$=Cl$^-$) the $\Phi$ was thus redetermined at an 18-fold lower concentration of $1.0\times10^{-4}$ M of reactant and found to be within experimental error of the value obtained at higher concentration at 14% conversions for duplicate runs. Due to the very low concentrations of the photoproduct 26 formed, it had to be quantified by absorption spectroscopy of the exposed photolysates without any workup. The product absorption at 432 nm was deconvoluted from the tailing absorption of reactant using Origin 8.6 software (OriginLab). After deconvolution, concentrations were obtained from a calibration curve constructed from known mixtures of reactant and product.

Computational Methods.

Density Functional Theory (DFT) calculations were performed using hybrid version of Perdew, Burke, and Ernzerhof density functional PBE0[33] in combination with a standard double-zeta quality 6-31G(d) basis set.[34] Solvent (water) effects were included using integral equation formalism polarizable continuum model (IEFPCM).[35-37] All calculated structures were tested for wavefunction stability. Geometry optimizations were performed without any geometric restraints followed by harmonic vibrational frequency calculations, and the nature of the transition structures found was verified by following the reaction path using intrinsic reaction coordinate (IRC).[38] Enthalpies and Gibbs free energies were calculated from these frequencies without applying any scaling factors. Only the enthalpies are shown in FIGS. 3 and 4 (vide supra). All calculations were performed with Gaussian 09 package.[39]

REFERENCES

1. H.-M. Lee, D. R. Larson and D. S. Lawrence, Illuminating the chemistry of life: design, synthesis, and applications of "caged" and related photoresponsive compounds, *ACS Chem. Biol.* 2009, 4, 409-427 and references cited therein.
2. G. Mayer and A. Heckel, Biologically active Molecules with a light switch, *Angew. Chem. Int. Ed.* 2006, 45, 4900-4921.
3. D. Warther, S. Gug, A. Specht, F. Bolze, J.-F. Nicoud, A. Mourot, M. Goeldner, Two-photon uncaging: new prospects in neuroscience and cellular biology, *Biorg. Med. Chem.* 2010, 18, 7753-7758.
4. M. Sarker, T. Shahrin and M. G. Steinmetz, Photochemical eliminations involving zwitterionic intermediates generated via electrocyclic ring closure of benzothiophene carboxanilides, *Org. Lett.* 2011, 13, 872-875.
5. (a) The nitrobenzyl group has been used as a photoremovable protecting group for sulfhydryl groups.[5b,c] It should be noted that the expected byproduct upon photochemical release of thiol is a nitrosoarene, and in general, nitrosoarenes undergo chemical reduction by thiols.[6] (b) C.-Y. Chang, T. T. Fernandez, R. Panchal and H. Bayley, Caged catalytic subunit of cAMP-dependent protein kinase, *J. Am. Chem. Soc.* 1998, 120, 7661-7662. (c) H. Bayley, C.-Y. Chang, W. T. Miller, B. Niblack and P. Pan, Caged peptides and proteins by targeted chemical modification, in *Methods in Enzymology,* 1998, 291, 117-135.
6. S. Montanari, C. Paradisi and G. Scorrano, Pathways of nitrosobenzene reduction by thiols in alcoholic media, *J. Org. Chem.* 1999, 64, 3422-3428.
7. A. Specht, S. Loudwig, L. Peng and M. Goeldner, p-Hydroxyphenacyl bromide as a photoremovable thiol label: a potential phototrigger for thiol-containing biomolecules, *Tetrahedron Lett.* 2002, 43, 8947-8950.
8. J. W. Walker, S. H. Gilbert, R. M. Drummond, M. Yamada, R. Sreekumar, R. E. Carraway, M. Ikebe and F. S. Fay, Signaling pathways underlying eosinophil cell motility revealed by using caged peptides", *Proc. Natl. Acad. Sci. USA,* 1998, 95, 1568-1573.
9. (a) H. Kimura, Hydrogen sulfide: its production, release, and functions, Amino Acids, 2011, 41, 113-121. (b) M. M. Gadalla and S. H. Snyder, Hydrogen sulfide as a gasotransmitter, *J. Neurochem.* 2010, 113, 14-26.
10. J. K. Moon, J. W. Park, W. S. Lee, Y. J. Kang, H. A. Chung, M. S. Shin, and Y. J. Yoon, Synthesis of Some 2-Substituted-thioxanthones, *J. Heterocyclic Chem.* 1999, 36, 793-798.
11. W. B. Wright and H. J. Brabander, The Preparation of 3-Chlorobenzo[b]thiophene Derivatives from Cinnamic Acids, *J. Heterocyclic Chem.* 1971, 8, 711-714.
12. Z. Pechlivanidis, H. Hopf and L. Ernst, Paracyclophanes: Extending the Bridges. *Synthesis, Eur. J. Org. Chem.* 2009, 223-237.
13. R. A. Delden, J. H. Hurenkamp and B. L. Feringa, Photochemical and Thermal Isomerization Processes of a Chiral Auxiliary Based Donor—Acceptor Substituted Chiroptical Molecular Switch: Convergent Synthesis, Improved Resolution and Switching Properties, *Chem. Eur. J.* 2003, 9, 2845-2853.
14. M. G. Neumann, M. H. Gehlen, M. V. Encinas, N. S. Allen, T. Corrales, C. Peinado and F. Catalina, Photophysics and Photoreactivity of Substituted Thioxanthones, *J. Chem. Soc., Faraday Transactions,* 1997, 93, 1517-1521.
15. Y. Ilichev, M. A. Schworer and J. Wirz, Photochemical reaction mechanisms of 2-nitrobenzyl compounds: methyl ethers and caged ATP, *J. Am. Chem. Soc.* 2004, 126, 4581-4595.
16. J. W. Walker, H. Martin, F. R. Schmitt, and R. J. Barsotti, Rapid release of an □-adrenergic receptor ligand from photolabile analogues, *Biochemistry,* 1993, 32, 1338-1345.
17. K. Stensrud, J. Noh, K. Kandler, J. Wirz, D. Heger, and R. S. Givens, Competing pathways in the photo-Favorskii rearrangement and release of esters: studies on fluorinated p-hydroxyphenacyl-caged GABA and glutamate phototriggers, *J. Org. Chem.* 2009, 74, 5219-5227.
18. R. S. Givens, J. F. W. Weber, A. H. Jung and C.-H. Park, New photoprotecting groups: desyl and p-hydroxyphenacyl phosphate and carboxylate esters, *Methods in Enzymology,* 1998, 120, 1-29.
19. V. Hagen, J. Bendig, S. Frings, T. Eckardt, S. Helm, D. Reuter and U. B. Kaupp, Highly efficient and ultrafast phototriggers for cAMP and cGMP by using long-wavelength UV/Vis-activation, *Angew. Chem. Int. Ed.* 2001, 40, 1045-1048.
20. T. Furuta, S. S.-H. Wang, J. L. Dantzker, T. M. Dore, W. J. Bybee, E. M. Callaway, W. Denk and R. Y. Tsien, *Proc. Natl. Acad. Sci, USA,* 1999, 96, 1193-1200.
21. M. J. Davis, C. H. Kragor, K. G. Reddie, H. C. Wilson, Y. Zue and T. M. Dore, Substituent effects on the sensitivity of a quinoline photoremovable protecting group to one- and two-photon excitation, *J. Org. Chem.* 2009, 74, 1721-1729.
22. (a) A. V. Pinheiro, A. J. Parola, P. V. Baptista, and J. C. Lima, pH Effect on the photochemistry of 4-methylcoumarin phosphate esters: caged-phosphate case study. *J. Phys. Chem. A.* 2010, 114, 12795-12803. (b) R. Schmidt, D. Geissler, V. Hagen, and J. Bendig, Mechanism of photocleavage of (coumarin-4-yl)methyl esters, *J. Chem. Phys.* 2007, 111, 5768-5774.
23. V. San Miguel, C. G. Bochet, and A. del Campo, Wavelength-selective caged surfaces: how many functional levels are possible? *J. Am. Chem. Soc.* 2011, 133, 5380-5388.
24. For a review of two-photon uncaging, see H. Kasai, M. Matsuzaki, and G. C. R. Ellis-Davies, Two-Photon Uncaging Microscopy, in *Imaging in Neuroscience and Development,* ed. R. Yuste and A. Konnerth, Cold Spring Harbor, N.Y., 2005, pp 275-383.
25. (a) With arylthiols efficient quenching[23a] of benzophenone by hydrogen transfer results in thiyl and ketyl radicals,[23b] which regenerate starting materials by disproportionation more rapidly than homocoupling to pinacol and disulfide.[23a-d] With mesitylmercaptan and benzophenone a quantum yield of 0.1 has been reported for disulfide formation.[23c] We did not observe disulfide or pinacol products in our study. A computational study indicates that such disporportionation will be facile.[23d] An alternate mechanism for quenching is electron transfer and rapid back electron transfer, which may be more important for alkylthiols than arylthiols[23b] (a) J. B. Guttenplan and S. G. Cohen, Quenching and reduction of photoexcited benzophenone by thioethers and mercaptans, *J. Org. Chem.* 1973, 38, 2001-2007. (b) S. Inbar, H. Linschitz, and S. G. Cohen, Quenching and radical formation in the reaction of photoexcited benzophenone with thiols and thioethers (sulfides). Nanosecond flash studies. *J. Am. Chem. Soc.* 1982, 104, 1679-1682. (c) S. G. Cohen, A. W. Rose, P. G. Stone, A. Ehret, Competitive processes in retardation by mercaptans of photoreduction by alcohols, *J. Am. Chem. Soc.* 1979, 101, 1827-1832. (d) H. Cardy, E. Poquet, M. Chaillet, and J. Ollivier, Ab intio CI study of hydrogen abstraction from hydrogen and methyl sulphide by ketone triplet excited state, *Chem. Phys.* 1993, 79-90.

26. J. Beltowski, Hypoxia in the renal medulla: implications for $H_2S$ signaling, *J. Pharmacol. Exp. Therapeutics,* 2010, 334, 358-363.

27. H. Zhao, H. Wang and M. Xian, Cysteine-activated hydrogen sulfide ($H_2S$) donors, *J. Am. Chem. Soc.* 2011, 133, 15-17.

28. (a) O. Rubio-Pons, L. Serrano-Andres, D. Burget and P. Jacques, A butterfly like motion as a clue to the photophysics of thioxanthone. *J. Photochem. Photobiol. A: Chem.* 2006, 179, 298-304. (b) X. Allonas, C. Ley, C. Bibaut, P. Jacques and J. P. Fouassier, Investigation of the triplet quantum yield of thioxanthone by time-resolved thermal lens spectroscopy: solvent and population lens effects, *Chem. Phys. Lett.* 2000, 322, 483-490.

29. (a) J. Seixas de Melo, L. M. Rodrigues, C. Serpa, L. G. Arnaut, I.C.F.R. Ferreira and M.-J. R. P. Queiroz, Photochemistry and Photophysics of Thienocarbazoles, *Photochem. Photobiol.* 2003, 77, 121-128. (b) B. Wex, B. R. Kaafarani, E. O. Danilov and D. C. Neckers, Altering the emission behavior with the turn of a thiophene ring: the photophysics of condensed ring systems of alternating benzenes and thiophenes, *J. Phys. Chem. A.* 2006, 110, 13754-13758.

30. C. Ma, M. G. Steinmetz, E. J. Kopatz, and R. Rathore, Photochemical cleavage and release of carboxylic acids from α-keto amides, *J. Org. Chem.* 2005, 70, 4431-4442.

31. C. Ma, Y. Chen, and M. G. Steinmetz, Photochemical cleavage and release of para-substituted phenols from α-keto amides. *J. Org. Chem.* 2006, 71, 4206-4215.

32. H. E. Zimmerman, Apparatus for quantitative and preparative photolysis. The Wisconsin black box, *Mol. Photochem.,* 1971, 3, 281-92.

33. J. P. Perdew, K. Burke, and M. Ernzerhof, Generalized gradient approximation made simple, *Phys. Rev. Lett.* 1996, 77, 3865-3868.

34. W. J. Hehre, L. Radom, P. v. R. Schleyer, J. A. Pople, Ab Initio Molecular Orbital Theory, John Wiley and Sons, New York, 1985.

35. G. Scalmani and M. J. Frisch, Continuous surface charge polarizable continuum models of solvation. I. General formalism, *J. Chem. Phys.,* 2010, 132, 114110.

36. J. Tomasi, B. Mennucci, and R. Cammi, Quantum mechanical continuum solvation models, *Chem. Rev.,* 2005, 105, 2999.

37. J. Tomasi, B. Mennucci, and E. Cancès, The IEF version of the PCM solvation method: An overview of a new method addressed to study molecular solutes at the QM ab initio level, *J. Mol. Struct.* (*Theochem*), 1999, 464, 211.

38. K. Fukui, The path of chemical reactions—the IRC approach, *Acc. Chem. Res.* 1981, 14, 363-368.

39. M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski and D. J. Fox, *Gaussian 09, Revision B.01,* Gaussian, Inc., Wallingford Conn., 2009.

We claim:

1. A compound having a formula:

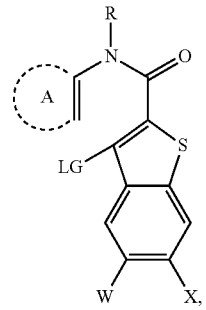

wherein W and X are hydrogen or —COOY, at least one of W and X is —COOY, and Y is hydrogen or $C_1$-$C_6$ alkyl;

$LG^-$ is $Cl^-$, $PhCH_2CO_2^-$, $PhS^-$, $PhCH_2S^-$, $PhO^-$, $HO^-$, or $HS^-$;

R is $C_1$-$C_6$ alkyl;

and A is a chromophore that is photochemically stimulated to react with the carbon atom bearing LG and photolyze LG from the compound, and A is a chromophore selected from a group consisting of thioxanthene-type chromophores having a structure

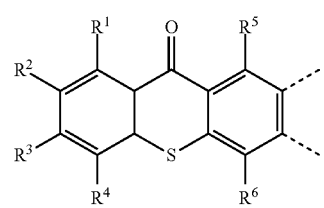

wherein $R^1$-$R^6$ are each independently hydrogen or halogen;

xanthene-type chromophores having a structure

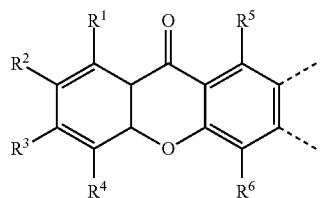

wherein $R^1$-$R^6$ are each independently hydrogen or halogen;

fluorescein-type chromophores having a structure

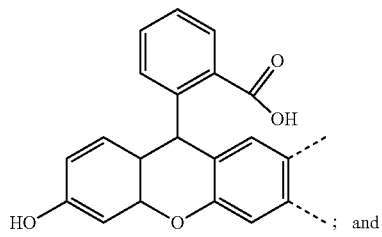

; and rhodamine-type chromophores having a structure

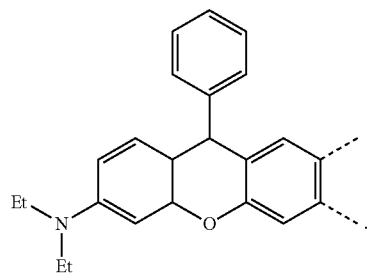

.

2. The compound of claim 1, having a formula:

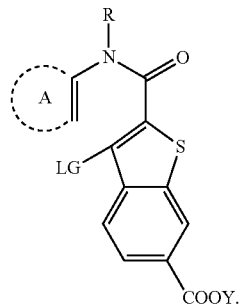

3. A compound having a formula:

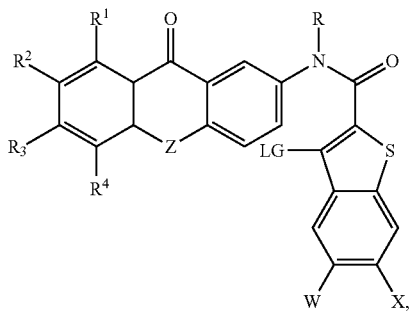

wherein Z is S or O;

$R^1$ is $C_1$-$C_6$ alkyl;

$R^1$, $R^2$, $R^3$, and $R^4$ are each independently halogen or hydrogen;

W and X are hydrogen or —COOY, at least one of W and X is —COOY, and Y is hydrogen or $C_1$-$C_6$ alkyl; and $LG^-$ is $Cl^-$, $PhCH_2CO_2^-$, $PhS^-$, $PhCH_2S^-$, $PhO^-$, $HO^-$, or $HS^-$.

4. The compound of claim 3, wherein Z is S.

5. The compound of claim 3, wherein W is hydrogen and X is a carboxyl group.

6. The compound of claim 3, wherein $R^2$ is halogen.

7. The compound of claim 6, wherein $R^2$ is bromine.

8. The compound of claim 3, wherein LG is chlorine.

9. The compound of claim 3, having a formula:

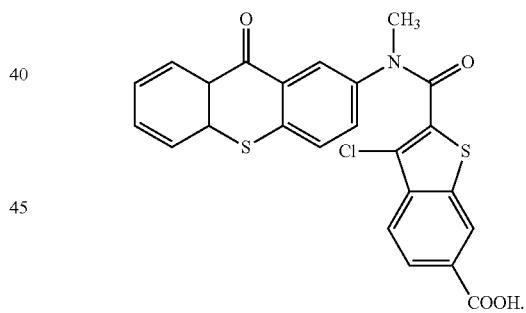

10. The compound of claim 3, having a formula:

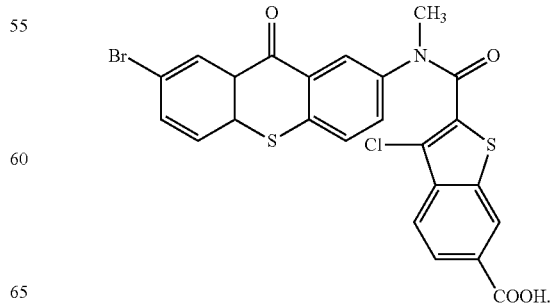

11. A compound having a formula:

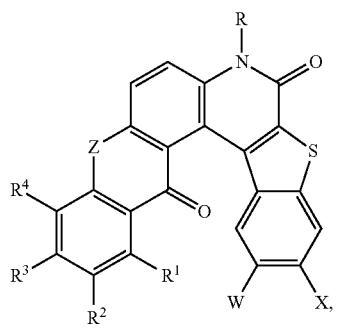

wherein Z is S or O;
R is $C_1$-$C_6$ alkyl;
$R^1$, $R^2$, $R^3$, and $R^4$ are each independently halogen or hydrogen;
W and X are hydrogen or —COOY, at least one of W and X is —COOY, and Y is hydrogen or $C_1$-$C_6$ alkyl.

12. The compound of claim 1, wherein the compound has an absorption maxima of about 350-400 nm.

13. The compound of claim 1, wherein the compound has an absorption maxima of about 400-450 nm.

14. A method for performing a photolytic reaction, the method comprising subjecting the compound of claim 1 to light to produce a compound having a formula:

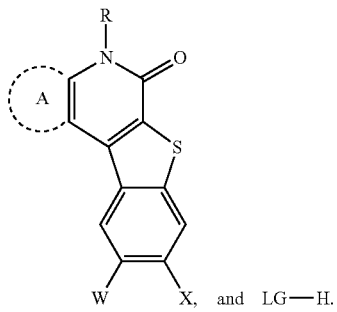

15. The method of claim 14, wherein the photolytic reaction has a yield of greater than about 90%.

16. A method for preparing the compound of claim 3, the method comprising reacting:
(a) a compound having a formula:

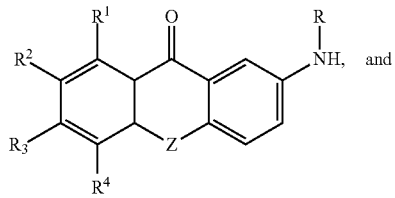

(b) a compound having a formula:

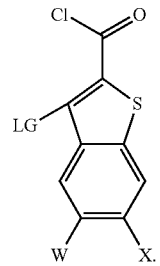

17. The method of claim 16, wherein $LG^-$ is $Cl^-$.

18. The method of claim 16, further comprising subjecting the reaction product to light.

* * * * *